US012135315B2

(12) United States Patent
Yamaki et al.

(10) Patent No.: US 12,135,315 B2
(45) Date of Patent: Nov. 5, 2024

(54) METHOD FOR ANALYZING METALLOPROTEIN IN BIOLOGICAL SAMPLE

(71) Applicant: Shimadzu Corporation, Kyoto (JP)

(72) Inventors: Satoshi Yamaki, Kyoto (JP); Yun Zou, Beijing (CN)

(73) Assignee: SHIMADZU CORPORATION, Kyoto (JP)

( * ) Notice: Subject to any disclaimer, the term of this patent is extended or adjusted under 35 U.S.C. 154(b) by 1035 days.

(21) Appl. No.: 17/047,216

(22) PCT Filed: Apr. 12, 2019

(86) PCT No.: PCT/JP2019/015950
§ 371 (c)(1),
(2) Date: Mar. 5, 2021

(87) PCT Pub. No.: WO2019/198811
PCT Pub. Date: Oct. 17, 2019

(65) Prior Publication Data
US 2021/0215650 A1    Jul. 15, 2021

(30) Foreign Application Priority Data

Apr. 13, 2018  (CN) .......................... 201810332262.6

(51) Int. Cl.
*G01N 30/74* (2006.01)
*G01N 30/02* (2006.01)
(Continued)

(52) U.S. Cl.
CPC ............. *G01N 30/74* (2013.01); *G01N 30/72* (2013.01); *G01N 30/88* (2013.01); *G01N 2030/027* (2013.01); *G01N 2030/065* (2013.01)

(58) Field of Classification Search
CPC ........ G01N 30/74; G01N 30/72; G01N 30/88; G01N 2030/027; G01N 2030/065; G01N 2030/8813; G01N 2030/8831
See application file for complete search history.

(56) References Cited

U.S. PATENT DOCUMENTS

2005/0035283 A1    2/2005  Hieftje et al.

FOREIGN PATENT DOCUMENTS

CA          2472271 A1    7/2003
JP       2005-514737 A    5/2005
(Continued)

OTHER PUBLICATIONS

Dean, John R., et al. "Studies of Metalloprotein Species by Directly Coupled High-performance Liquid Chromatogrpahy Inductively Coupled Plasma Mass Spectrometry", Journal of Analytical Atomic Spectrometry, Sep. 1987, vol. 2. (Year: 1987).*
(Continued)

*Primary Examiner* — Paul M. West
(74) *Attorney, Agent, or Firm* — Muir Patent Law, PLLC

(57) ABSTRACT

The present invention relates to a method for analyzing a metalloprotein in a biological sample capable of continuously maintaining conditions of LC-ICPMS constant to measure a metalloprotein with high data reliability. The method for analyzing a metalloprotein which is a complex in a biological sample, the metalloprotein being a complex in which a biomolecule and a metal element bind to each other, includes: treating a biological sample which has been subjected to a pretreatment by liquid chromatography to separate the metalloprotein, and analyzing the separated metalloprotein by inductively coupled plasma mass spectrometry, wherein an ammonium acetate solution is used as a mobile phase.

7 Claims, 23 Drawing Sheets

(51) Int. Cl.
    *G01N 30/06*     (2006.01)
    *G01N 30/72*     (2006.01)
    *G01N 30/88*     (2006.01)

(56) References Cited

FOREIGN PATENT DOCUMENTS

| JP | 2009-114105 A | 5/2009 |
|---|---|---|
| WO | 2003/058204 A2 | 7/2003 |

OTHER PUBLICATIONS

Kodali, Phanichand, et al. "Detection of metals and metalloproteins in the plasma of stroke patients by mass spectrometry methods", Metallomics, Oct. 2012; 4(10): 1077-1087. (Year: 2012).*

Written Opinion of the International Searching Authority (ISA237) dated Jul. 16, 2019 for PCT application No. PCT/JP2019/015950, submitted with a machine translation.
Lopez-Avila et al., "Determination of Ceruloplasmin in Human Serum by Immunoaffinity Chromatography and Size-Exclusion Chromatography-ICP-MS", Agilent Application Note, Publication No. 5989-5304EN, May 31, 2017, pp. 1-10, (retrieval date Jun. 22, 2019, Internet: URL: <https://www.agilent.com/cs/library/applications/5989-5304EN.pdf>).
Second Office Action dated Mar. 2, 2022 for corresponding Chinese Application No. CN201810332262.6.
Decision of Rejection dated Jun. 1, 2022 for corresponding Chinese Patent Application No. CN 201810332262.6 with machine translation.
First Office Action for Chinese patent application No. 201810332262.6 dated Sep. 2, 2021, submitted with a machine translation.
Lopez Avila et al, "Determination of ceruloplasmin in human serum by SEC-ICPMS", Anal Bioanal Chem (2006) 386: 180-187, Jun. 23, 2006.

* cited by examiner

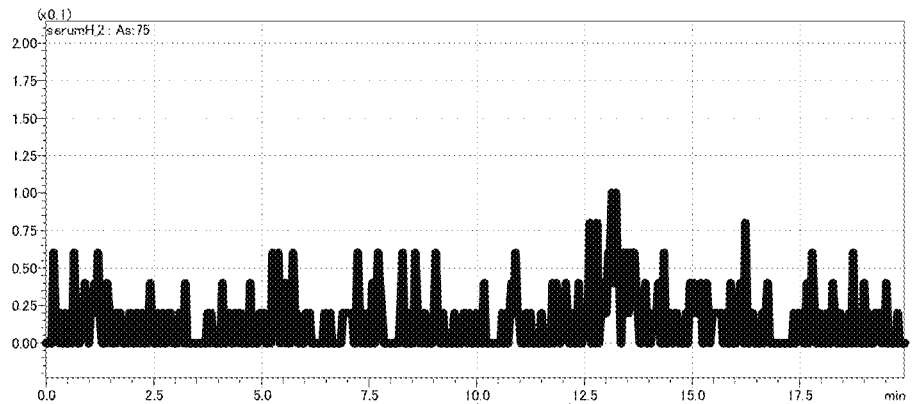
FIG. 19
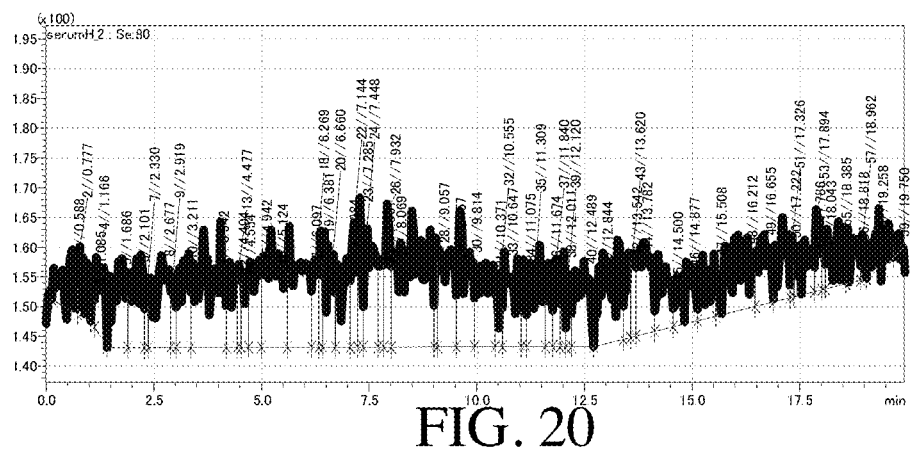
FIG. 20
FIG. 21

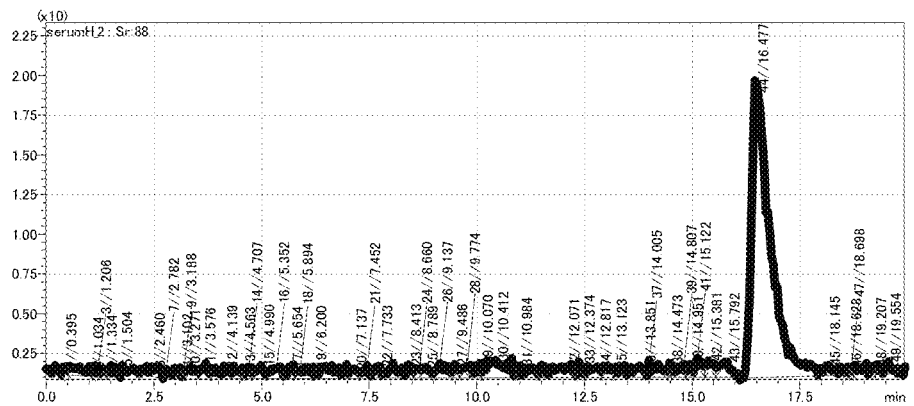
FIG. 22
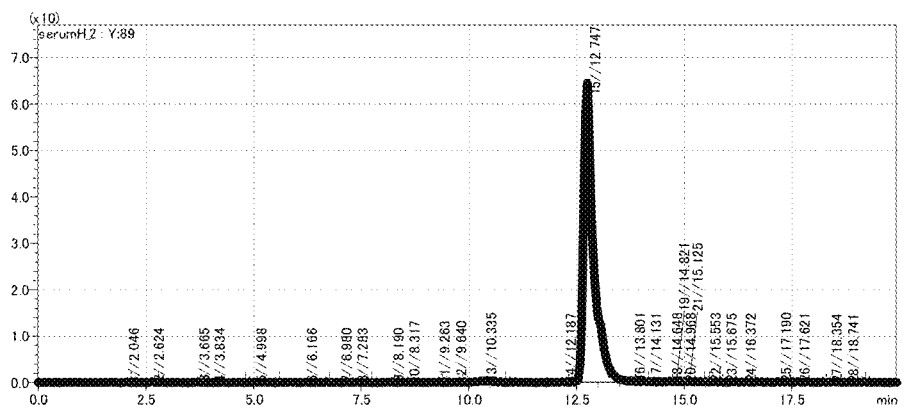
FIG. 23
FIG. 24

(i)

(j)

(k)

(l)

(a)

(b)

(a)

(b)

METHOD FOR ANALYZING METALLOPROTEIN IN BIOLOGICAL SAMPLE

TECHNICAL FIELD

The present invention relates to a method for analyzing a metalloprotein in a biological sample, and more particularly, to a method for analyzing a metalloprotein in a biological sample using liquid chromatography-inductively coupled plasma mass spectrometry (LC-ICPMS).

BACKGROUND OF THE INVENTION

Trace elements play an important role in a biological system in plants and animals. As shown in recent studies, the amount of metal in an organism relates to certain pathological elements. As a method for detecting a metal element from a sample to estimate its content, inductively coupled plasma mass spectrometry (ICPMS) is one of the highly efficient and convenient ways.

In an organism, biomolecules, such as, e.g., enzymes and porphyrins, binds to a metal to form a complex called a metalloprotein. For such a complex, a method is known in which ceruloplasmin in human serum is measured by combining liquid chromatography (LC) and inductively coupled plasma mass spectrometry (ICPMS) (see Non-Patent Document 1). Organometallic compounds of arsenic, tin, and mercury have also been analyzed in environmental studies.

PRIOR ART DOCUMENT

Non-Patent Document

Non-Patent Document 1: Determination of Ceruloplasmin in Human Serum by Immunoaffinity Chromatography and Size Exclusion Chromatography-ICP-MS, Viorica Lopez-Avila et al. <<Springer>>, 2004: 245-468

SUMMARY OF THE INVENTION

Problems to be Solved by the Invention

In the method of Non-Patent Document 1, a Tris-HCl buffer (a mixture of trishydroxymethylaminomethane and hydrochloric acid) having a flow rate of 0.6 mL/min at a concentration of 50 mM is used as a mobile phase of liquid chromatography (LC). This buffer is widely used for ICPMS measurement.

However, the Tris-HCl buffer used in Non-Patent Document 1 is a nonvolatile solution. When performing an LC-ICPMS analysis, the solute in this buffer precipitates as a nonvolatile solid at a high-temperature ion source. After multiple analyses, there is a possibility that the accumulation of solids described above blocks the skimmer, resulting in the sampling interruption. Under the circumstance, in the prior art, in order to avoid clogging of the skimmer, the analysis must be frequently interrupted in the course of the analysis to perform the apparatus maintenance to remove the deposited components at an early stage.

In an omics analysis, the number of samples is very large. Therefore, it is desirable to provide an apparatus and a method capable of performing measurement stably and continuously over a long period. However, in the above-described technical proposal, due to the frequent interruptions and maintenance, the condition of the apparatus cannot be maintained constant during a series of multiple sample analyses. For this reason, there has been a problem that measurement data of a metalloprotein in a biological sample is not reliable.

Means for Solving the Problem

The present invention has been made to solve the above-described problems. The present invention provides a method for analyzing a metalloprotein in a biological sample, the metalloprotein being a complex in which a biomolecule and a metal element bind to each other, the method comprising:
  treating the biological sample that has been subjected to a pretreatment by liquid chromatography to separate the metalloprotein; and
  analyzing the separated metalloprotein by inductively coupled plasma mass spectrometry,
  wherein an ammonium acetate solution is used as a mobile phase.

In the method for analyzing a metalloprotein in a biological sample as described above, the liquid chromatography is preferably size exclusion chromatography.

In the method for analyzing a metalloprotein in a biological sample as described above, the separated metalloprotein is preferably detected by a UV detector before performing an analysis of the separated metalloprotein by the inductively coupled plasma mass spectrometry.

In the method for analyzing a metalloprotein in a biological sample as described above, a concentration of the ammonium acetate solution is preferably 25 mM to 100 mM.

In the method for analyzing a metalloprotein in a biological sample as described above, a pH value of the ammonium acetate solutions is preferably between 6 and 7.

In the method for analyzing a metalloprotein in a biological sample as described above, immunoaffinity chromatography is preferably used in the pretreatment.

In the method for analyzing a metalloprotein in a biological sample as described above, the metal element is preferably K, P, Na, Ca, Mg, Al, As, Hg, Pb, Cd, Ti, Ag, Ba, Zn, Cr, Mn, Cu, Rb, Fe, Ge, Se, Sr, Co, Ni, Mo, Sn, Sb, Pt, Cs, U, La, Ce, Pr, Nd, Sm, Eu, Gd, Tb, Dy, Ho, Er, Tm, Yb, Lu, Y, Li, or B.

In the method for analyzing a metalloprotein in a biological sample as described above, the separated metalloprotein is preferably further analyzed by electrospray ionization mass spectrometry when analyzing by the inductively coupled plasma mass spectrometry.

Effects of the Invention

By adopting the method for analyzing a metalloprotein in a biological sample according to the present invention, it is possible to continuously perform measurement without interruption, and measurement of a metalloprotein can be performed with high data reliability while maintaining the condition of liquid chromatography-inductively coupled plasma mass spectrometry (LC-ICPMS) constant.

BRIEF DESCRIPTION OF THE DRAWINGS (a) to (d) of FIG. 1 are chromatograms of two elements, Fe and Co, measured in Example 1.

FIG. 19 is a chromatogram of specified 47 types of elements measured in Example 2.

FIG. 20 is a chromatogram of specified 47 types of elements measured in Example 2.

FIG. 21 is a chromatogram of specified 47 types of elements measured in Example 2.

FIG. 22 is a chromatogram of specified 47 types of elements measured in Example 2.

FIG. 23 is a chromatogram of specified 47 types of elements measured in Example 2.

FIG. 24 is a chromatogram of specified 47 types of elements measured in Example 2.

Figure 49A:
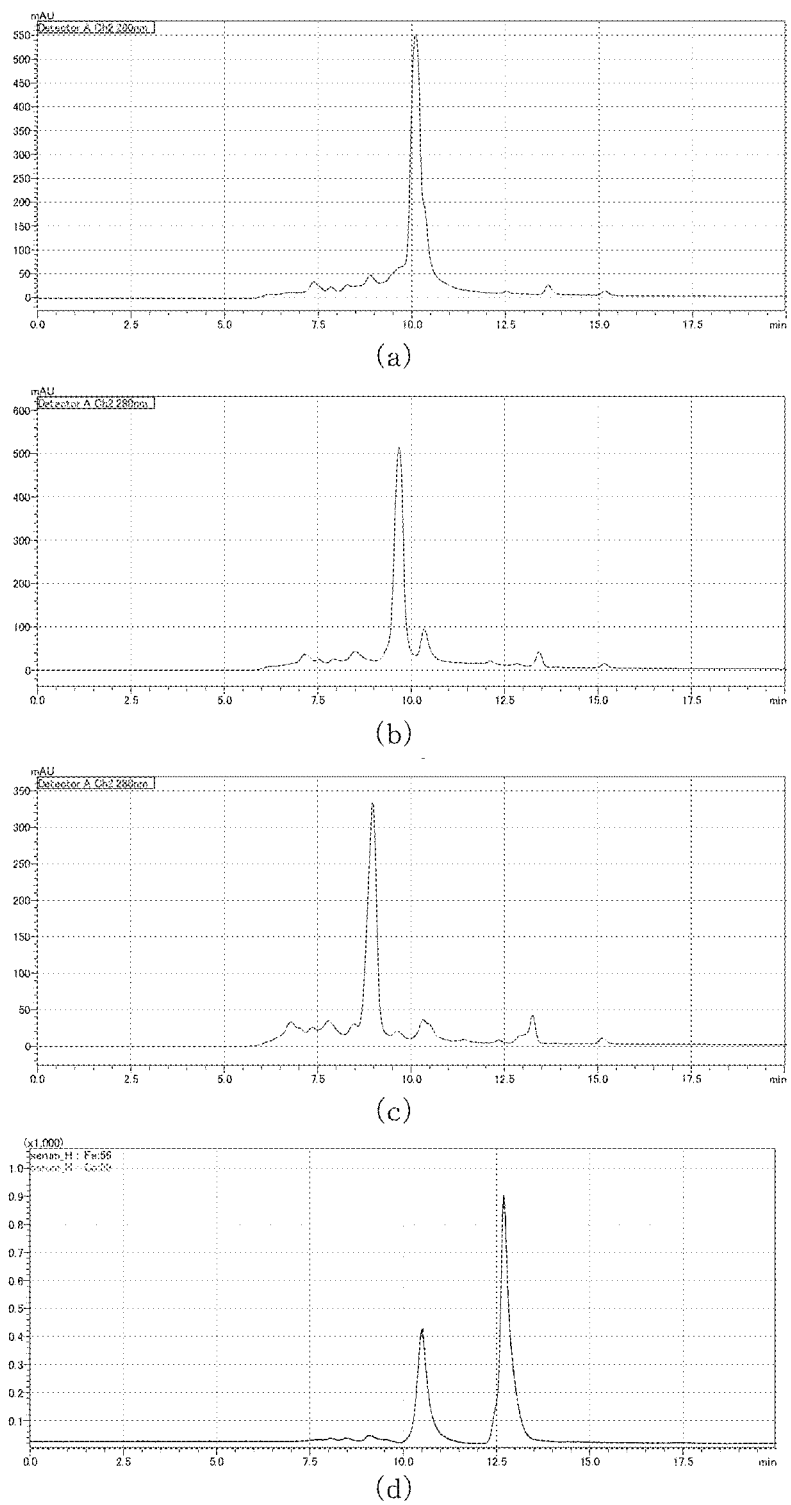

(a) to (d) of FIG. 49A are chromatograms of two elements, Fe and Co, measured at varying concentrations of the mobile phase in Example 3.

Figure 49B:
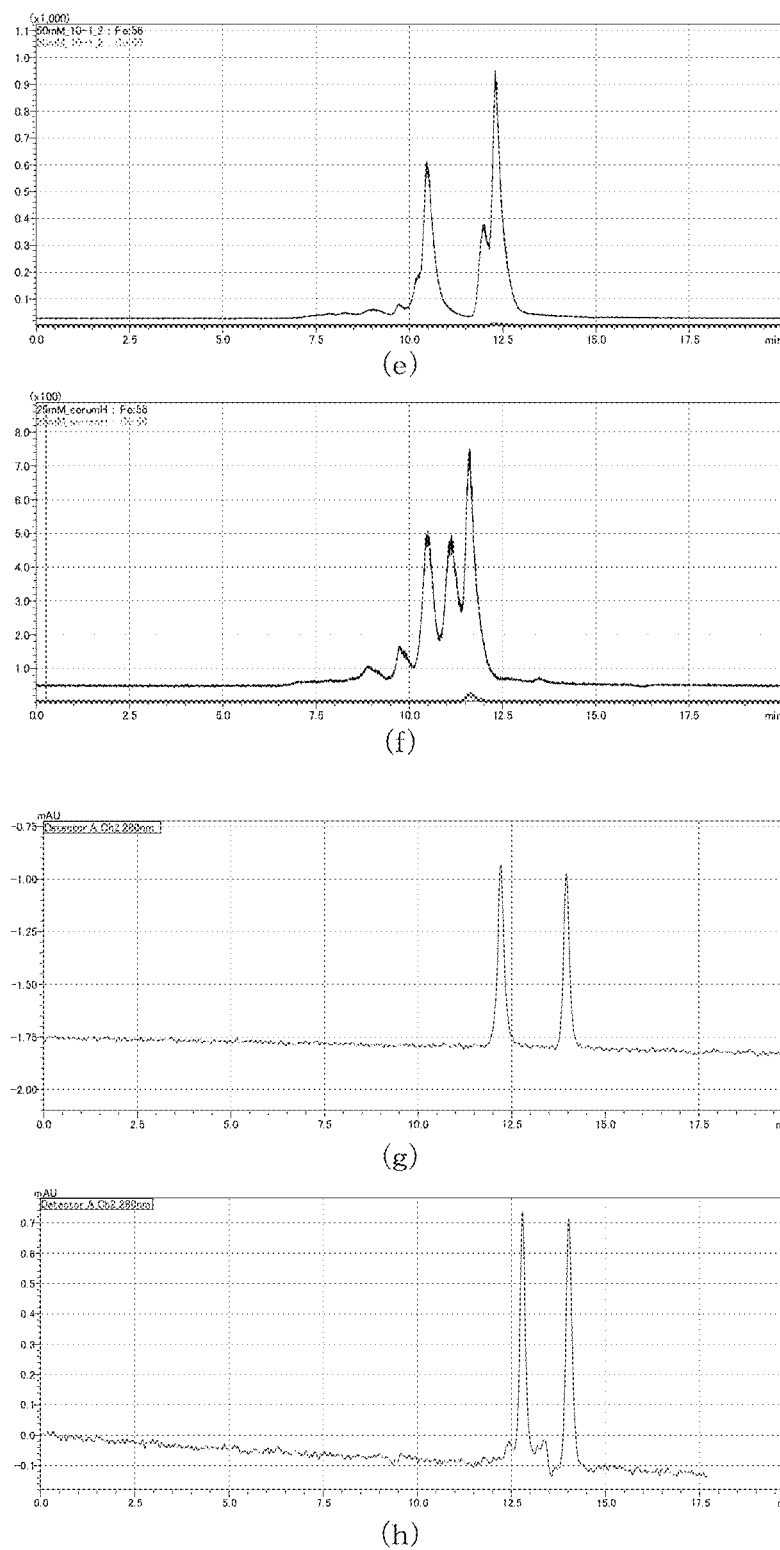

(e) to (h) of FIG. 49B are chromatograms of two elements, Fe and Co, measured at varying concentrations of the mobile phase in Example 3.

Figure 49C:
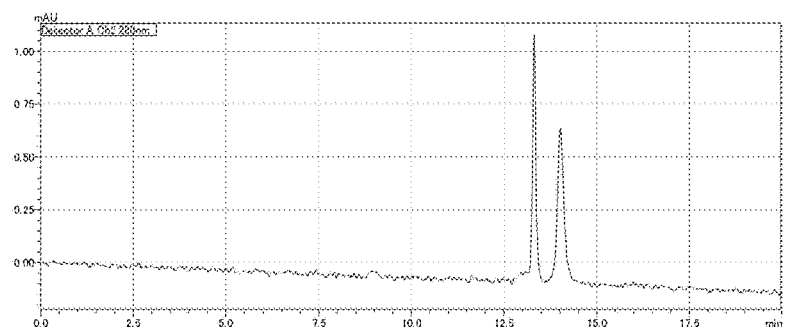
Figure 49C:
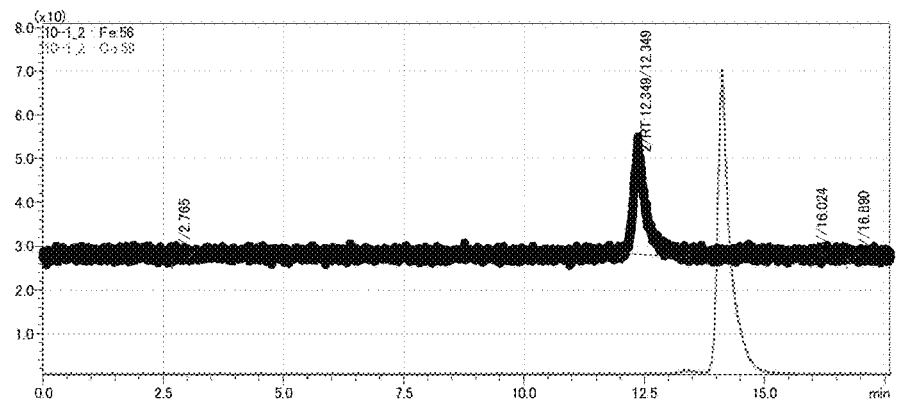
Figure 49C:
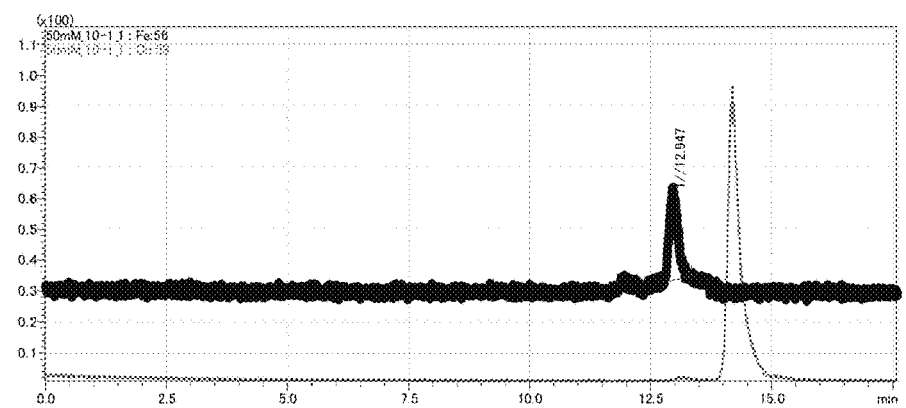
Figure 49C:
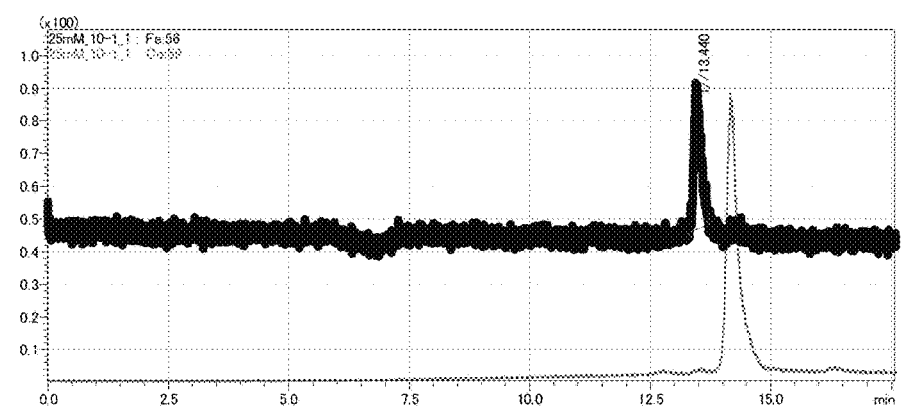

(i) to (l) of FIG. 49C are chromatograms of two elements, Fe and Co, measured at varying concentrations of the mobile phase in Example 3.

Figure 50:
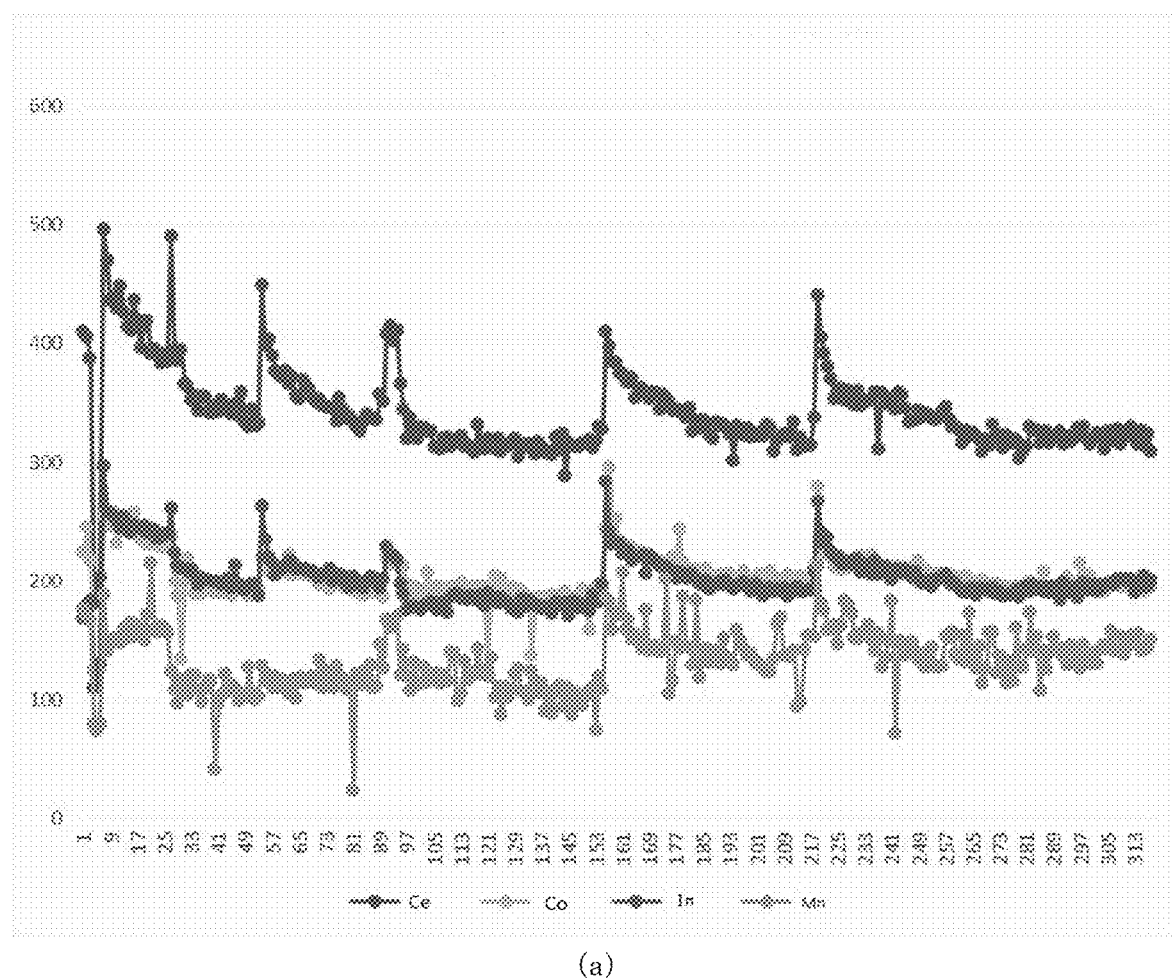
Figure 50:
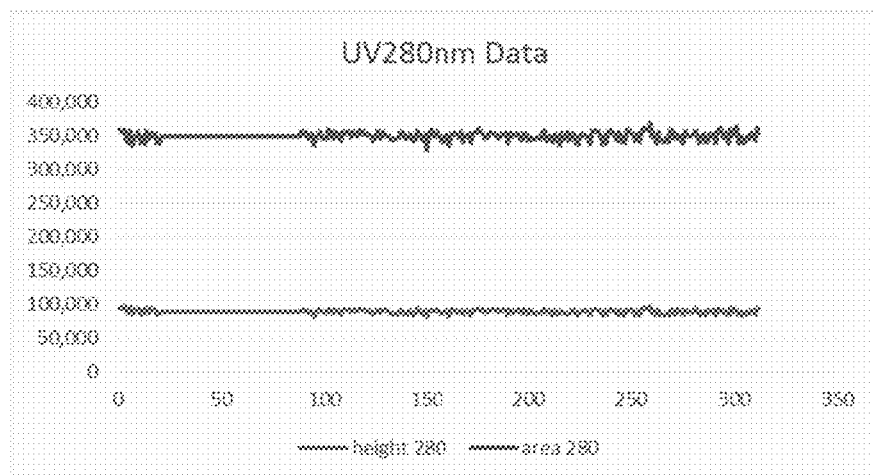

(a) and (b) of FIG. 50 are analytical diagrams showing the consecutive operation results of LC-ICPMS in Example 4.

Figure 51A:
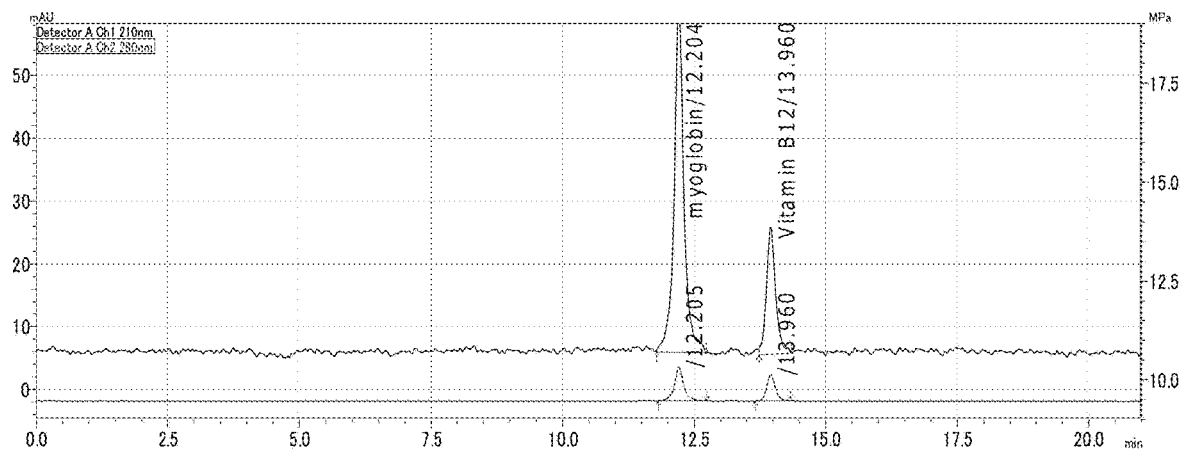
Figure 51A:
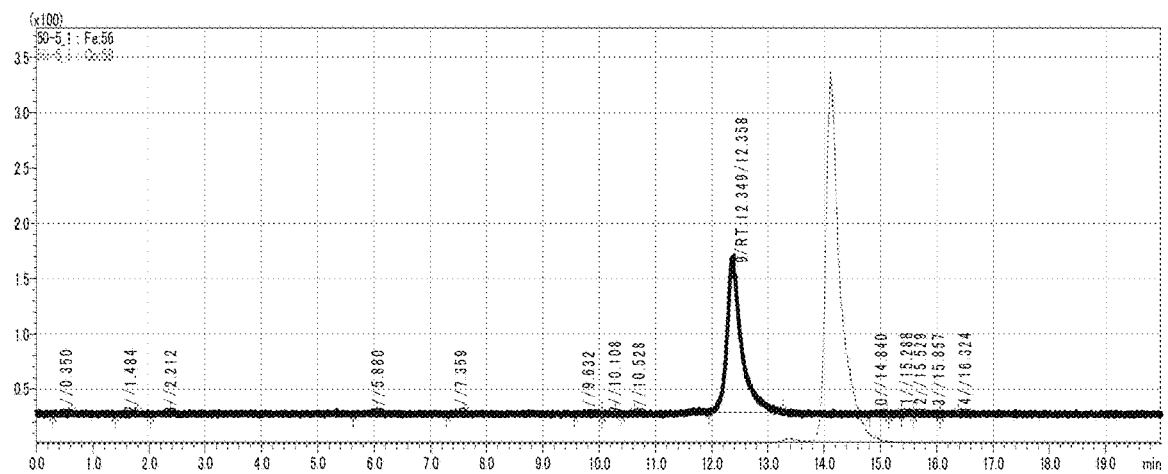

(a) and (b) FIG. 51A show LC-UV-ICPMS chromatograms of a standard sample of Example 4 and the calibration curve.

Figure 51B:
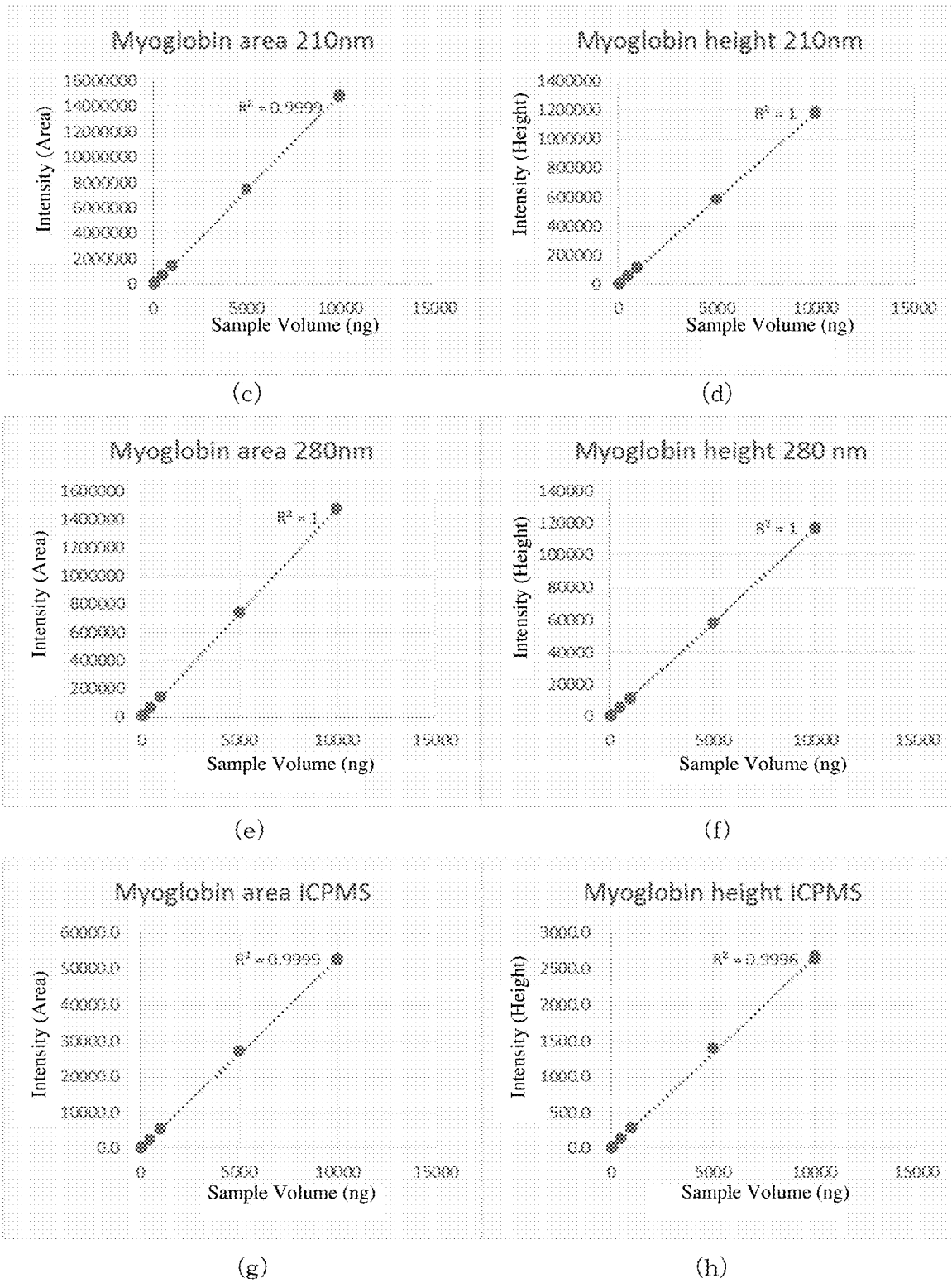

(c) to (h) of FIG. 51B show LC-UV-ICPMS chromatograms of a standard sample of Example 4 and the calibration curve.

Figure 51C:
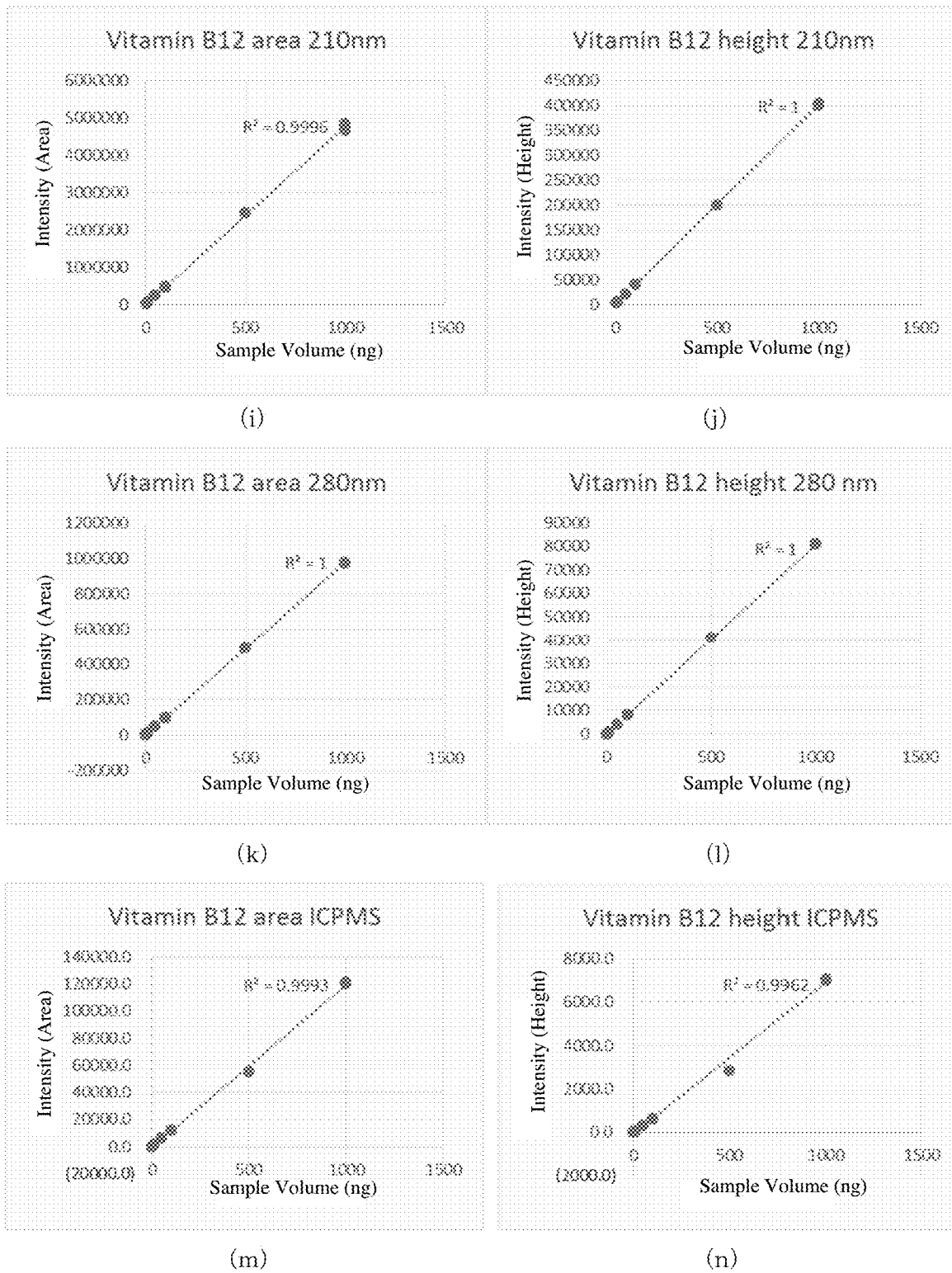

(i) to (n) of FIG. 51C show LC-UV-ICPMS chromatograms of a standard sample of Example 4 and the calibration curve.

EMBODIMENTS FOR CARRYING OUT THE INVENTION

The method for analyzing a metalloprotein in a biological sample according to the present invention is a method that performs an analysis using LC-ICPMS in the same manner as in prior art. In order to avoid blockage of a skimmer by deposited solids, a volatile ammonium acetate solution is used as the mobile phase. With this, in the present invention, it is possible to continuously analyze a biological sample without requiring frequent apparatus maintenance and maintain the condition of the analysis constant to ensure data reliability.

Specifically, according to the analysis method of this embodiment, initially, a pretreatment is performed on a biological sample. In the pretreatment, it is preferable to remove several types of proteins high in content, such as, e.g., albumin, IgG, transferrin, IgA, haptoglobin, and antitrypsin, by immunoaffinity chromatography. These macromolecule proteins are often indistinguishable from metalloproteins by SEC (size exclusion chromatography), which will be described later. The use of immunoaffinity chromatography enables the avoidance of interference by these proteins.

Thereafter, the biological sample that has been subjected to the pretreatment is processed to separate the metalloprotein by liquid chromatography. The use of the size exclusion chromatography (SEC) enables the separation of metalloproteins and free metal elements.

Next, the separated metalloproteins are analyzed by inductively coupled plasma mass spectrometry (ICPMS) to determine the type and content. In this embodiment, it is preferred to further detect metalloproteins after LC by a UV detector before performing the analysis by ICPMS. As an advantage to do this, in cases where the detection signal of the ICPMS is abnormally attenuated, by comparing the detection signal of the UV detector with the detection signal of the inductively coupled plasma mass spectrometry (ICPMS), it is possible to determine whether the liquid chromatography (LC) is failed or the inductively coupled plasma mass spectrometry (ICPMS) is failed, e.g., whether the skimmer is blocked. For example, in cases where the detection result of the UV detector is normal and the detection result of the inductively coupled plasma mass spectrometry (ICPMS) is obviously attenuated, it can be determined that it is a failure of the inductively coupled plasma mass spectrometry (ICPMS). On the other hand, in cases where both the detection result of the UV detector and that of the inductively coupled plasma mass spectrometry (ICPMS) are abnormally attenuated or not detected, it can be determined that the failure of the liquid chromatography (LC).

Note that it is also possible to analyze the separated metalloprotein using electrospray ionization mass spectrometry (ESIMS) when analyzing the metalloprotein separated by inductively coupled plasma mass spectrometry (ICPMS) at the same time. The analysis by the inductively coupled plasma mass spectrometry (ICPMS) reveals which types of metal elements are contained in this metalloprotein. The electrospray ionization mass spectrometry (ESIMS) can measure the molecular weight of this metalloprotein. The combination thereof enables to specify this metalloprotein.

Note that performing the size exclusion chromatography (SEC) under mild conditions (close to the biological environment) not only maintains the protein in its native state but also provides the approximate molecular size information. Therefore, in the liquid chromatography (LC), the pH value of the ammonium acetate solution is preferably 6 to 7.

The feasibility and the data reliability when using an ammonium acetate solution as a mobile phase in a method for analyzing a metalloprotein LC-ICPMS will be described by exemplifying four examples.

Example 1

In this Example, two elements of Fe and Co were measured, and the concentration of the mobile phase was set to 100 mM.

As the biological sample, a mixed solution of a commercially available sample A: SIGMA Human Serum H4522 (containing Fe elements) and a commercially available sample B: Wako Cyanocobalamin, C63H88CoN14O14P, MW 1355. 38 (vitamin B12, VB12) (containing Co elements), SIGMA Myoglobin (obtained from horse hearts), and MW 17 kDa (containing Fe elements), was adopted. All parts which come into contact with the solution were made of metal-free materials.

The LC-ICPMS analysis conditions of this Example are shown in Tables 1-1 and Table 1-2 shown below.

TABLE 1-1

| Apparatus used: | Shimadzu High-Speed liquid chromatograph LC-20 Inert High-Pressure GE System |
|---|---|
| | System Controller | CBM-20Alite |
| | Liquid feed unit | LC-20Ai |
| | On-line deaeration unit | DGU-20A$_{5R}$ |
| | Auto-sampler | SIL-20AC + SIL inert kit |
| | Column-oven | CTO-20AC |
| | Mixer | Mixer PEEK 1.6 mL |
| | UV detector | SPD-20AV + semi micro cell |
| | ICPMS | ICPMS-2030 |
| | LC-workstation | LabSolutions Ver. 5.82 sp1 |
| | ICPMS Workstation | LabSolutions ICPMS TRM Ver. 1.02 |

TABLE 1-2

| LC-ICPMS Analysis Conditions | |
|---|---|
| Column | Phenomenex Yarra SEC-X300 (300 mmL. × 4.6 mm I.D., 1.8 µm) |
| Mobile phase | 100 mmol/L aqueous ammonium acetate solution, near pH 6 |
| Mobile phase flow rate | 0.3 mL/min (pressure 18.2 MPa) |
| Column temperature | 35° C. |
| Injection volume | 10 µL (SIL wash solution: water) |
| Sample | SIGMA Human Serum H4522-100 ML All samples were filtered and diluted 2 times with 10 mM ammonium acetate-water Wako Cyanocobalamin, C63H88CoN14O14P, MW 1355.38 (Vitamin B12, VB12) SIGMA Myoglobin from equine heart, MW 17 kDa Dissolve in the mobile phase |
| Detector | Shimadzu UV detector SPD-20AV Semi-micro temperature control cell Lamp: D$_2$ Wavelength: 210, 280 nm Sampling: 2 Hz Cell temperature: 40° C. Capture time: 21 min |
| ICPMS | See FIG. 1-1 Capture time: 20 min |

| Detected ion: | element m/z | Dwell time (sec) |
|---|---|---|
| Fe | 56 | 0.1 |
| Co | 59 | 0.1 |

| Measurement time | 21 min |
|---|---|

Figure 1:
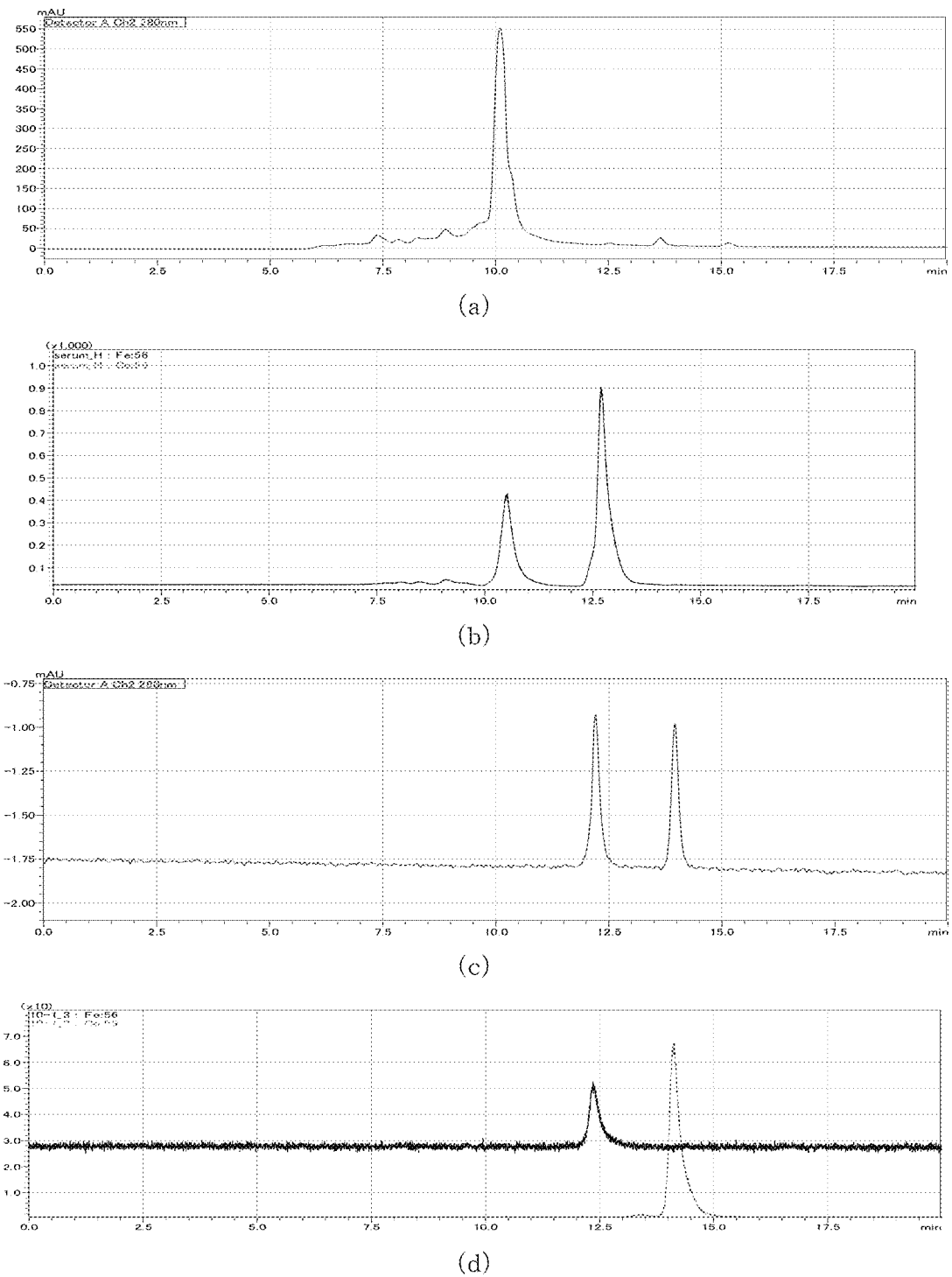

The results of the analyses are shown in FIG. 1. (a) of FIG. 1 shows the signal of the metalloprotein when the sample A was subjected to liquid chromatography (LC). The signal was detected by a UV detector with the sample irradiated with 280 nm light. (b) of FIG. 1 shows the signal of the metalloprotein when the sample A was subjected to liquid chromatography (LC). The signal was detected by inductively coupled plasma mass spectrometry (ICPMS). (c) of FIG. 1 shows the signal of the metalloprotein when the sample B was subjected to liquid chromatography (LC). The signal was detected by a UV detector with the sample irradiated with 280 nm light. (d) of FIG. 1 shows the signal of the metalloprotein when the sample B was subjected to liquid chromatography (LC). The signal was detected by inductively coupled plasma mass spectrometry (ICPMS).

The two peaks in (b) of FIG. 1 show proteins containing two types of irons, and no protein containing cobalt was detected. The two peaks in (c) of FIG. 1 indicate two components in the sample B. The two peaks in (d) of FIG. 1 indicate the metal elements Fe and Co.

Example 2

LC-ICPMS (Liquid chromatography-Inductively coupled plasma mass spectrometry) using an ammonium acetate solution as a mobile phase can analyze all known types of metalloproteins. In this Example, 47 types of metal elements among them were analyzed and measured, but the measurable ranges are not limited thereto. The sample A is adopted as a biological sample, and the concentration of the mobile phase was set to 100 mM.

The apparatus used in this Example is the same as that used in Example 1. The analysis conditions of LC-ICPMS are shown in Table 2 shown below.

TABLE 2

| Column | Phenomenex Yarra SEC-X300 (300 mmL. × 4.6 mm I.D., 1.8 μm) |
|---|---|
| Mobile phase | 100 mmol/L Aqueous ammonium acetate solution, near pH 6 |
| Mobile phase flow rate | 0.3 mL/min (pressure 18.2 MPa) |
| Column temperature | 35° C. |
| Injection volume | 10 μL (SIL wash solution: water) |
| Sample | SIGMA Human Serum H4522-100 ML All samples were filtered and diluted 2 times with 10 mM ammonium acetate-water |
| Detector | Shimadzu UV detector SPD-20AV Semi-micro temperature control cell Lamp: D₂ Wavelength: 210, 280 nm Sampling: 2 Hz Cell temperature: 40° C. Capture time: 21 min |
| ICPMS | Capture time: 20 min Detected ion: element K, P, Na, Ca, Mg, Al, As, Hg, Pb, Cd, Ti, Ag, Ba, Zn, Cr, Mn, Cu, Rb, Fe, Ge, Se, Sr, Co, Ni, Mo, Sn, Sb, Pt, Cs, U, La, Ce, Pr, Nd, Sm, Eu, Gd, Tb, Dy, Ho, Er, Tm, Yb, Lu, Y, Li, B. Dwell time (sec) each 0.05 |
| Measurement time | 21 min |

ICPMS analysis results of these 47 elements are shown in FIG. 2 to FIG. 48.

Example 3

In this Example, two elements of Fe and Co were measured. As biological samples, the sample A and the sample B were adopted, respectively, and the concentrations of the mobile phases were set to 100 mM, 50 mM, and 25 mM, respectively.

The apparatus used in this Example was the same as that used in Example 1. LC-ICPMS analytical conditions are shown in Table 3 shown below.

TABLE 3

| Column | Phenomenex Yarra SEC-X300 (300 mmL. × 4.6 mm I.D., 1.8 μm, MW range 10k-700 kDa) |
|---|---|
| Mobile phase | 100 mmol/L aqueous ammonium acetate solution, near pH 6 50 mmol/L aqueous ammonium acetate solution, near pH 6 25 mmol/L aqueous ammonium acetate solution, near pH 6 |
| Mobile phase flow rate | 0.3 mL/min (pressure 18.2 MPa) |
| Column temperature | 35° C. |
| Injection volume | 10 μL (SIL wash solution: water) |

TABLE 3-continued

| Sample | SIGMA Human Serum H4522-100 ML All samples were filtered and diluted 2 times with 10 mM ammonium acetate-water and Wako Cyanocobalamin, C63H88CoN14O14P, MW 1355.38 (Vitamin B12, VB12) SIGMA Myoglobin from equine heart, MW 17 kDa Dissolve in the mobile phase | | |
|---|---|---|---|
| Detector | Shimadzu UV detector SPD-20AV Semi-micro temperature control cell Lamp: D₂ Wavelength: 210, 280 nm Sampling: 2 Hz Cell temperature: 40° C. Capture time: 21 min | | |
| ICPMS | See FIG. 2-2 Capture time: 20 min | | |
| | Detected ion: | element m/z | Dwell time (sec) |
| | Fe | 56 | 0.100 |
| | Co | 59 | 0.100 |
| Measurement time | 21 min | | |

The analysis results are shown in FIG. 49. (a) to (c) of FIG. 49 show the signal of the metalloprotein when the sample A was subjected to liquid chromatography (LC). The signal was detected by the UV detector with the sample irradiated with 280 nm light. The concentrations of the mobile phases in (a) to (c) of FIG. 49 were 100 mM, 50 mM, and 25 mM, respectively. (d) to (f) of FIG. 49 show the signal of the metalloprotein when the sample A was subjected to liquid chromatography (LC). The signal was detected by ICPMS. The concentrations of the mobile phases in (d) to (f) of FIG. 49 were 100 mM, 50 mM, and 25 mM, respectively. (g) to (i) of FIG. 49 show the signal of a metalloprotein when the sample B was subjected to liquid chromatography (LC). The signal was detected by the UV detector with the sample irradiated with 280 nm light. The concentrations of the mobile phases in (g) to (i) of FIG. 49 were 100 mM, 50 mM, and 25 mM, respectively. (j) to (l) of FIG. 49 show the signal of the metalloprotein when the sample B was subjected to liquid chromatography (LC). The signal was detected by ICPMS. The concentrations of the mobile phases in (j) to (l) of FIG. 49 were 100 mM, 50 mM, and 25 mM, respectively.

Example 4

The apparatus used in this Example is the same as that used in Example 1. As described above, the use of ammonium acetate solution as the mobile phase enables continuous analyses of many samples without interruption for maintenance. In this Example, ICPMS standard samples were continuously measured over 300 times by flow injection in order to confirm the accuracy of ICPMS data when an ammonium acetate solution was used as the mobile phase. The measurement results are shown in FIG. 50. The LC-ICPMS analysis conditions of the measurements in FIG. 50 are shown in Table 4 shown below.

TABLE 4

| Mobile phase | 100 mmol/L aqueous ammonium acetate solution, near pH 6 |
|---|---|
| Mobile phase flow rate | 0.50 mL/min |
| Column temperature | Room temperature |
| Injection volume | 10 μL (SIL wash solution: water) |

TABLE 4-continued

| | |
|---|---|
| Sample | ICPMS standard samples; Be 1 ppb, Co and Mn 0.5 ppb, In and Bi and Ce 0.2 ppb in 1% (0.14 mol/L) HNO$_3$ |
| Detector | Shimadzu UV detector SPD-20AV Semi-micro temperature control cell |
| | Lamp: D$_2$ |
| | Wavelength: 210, 280 nm |
| | Sampling: 2 Hz |
| | Cell temperature: 40° C. |
| | Capture time: 15 min |
| ICPMS | See FIG. 2-2 |
| | Capture time: 14 min |

| Detected ion: | element m/z | Dwell time (sec) |
|---|---|---|
| Ce | 140 | 0.100 |
| Co | 59 | 0.100 |
| In | 115 | 0.100 |
| Mn | 55 | 0.100 |

| | |
|---|---|
| Measurement time | 15 min |

(a) of FIG. 50 shows the peak area of the ICPMS chromatogram obtained for each sample injection analysis in 300 or more analyses. The horizontal axis shows the number of injections, and the vertical axis shows the peak area. (b) of FIG. 50 shows the detection results (peak height and peak area) of the connected UV detector in these 300 or more analyses. As can be seen from FIG. 50, the data reproducibility is good by performing uninterrupted continuous measurements with an ammonium acetate solution as a mobile phase, and thus the reliability is high.

On the other hand, the sample B was measured at the analysis conditions shown in Table 5, and the peak area and the peak height of the chromatogram at different injection amounts were acquired and shown in FIG. 51. (a) and (b) of FIG. 51 show the detection results of the UV detector and the ICPMS, respectively, and (c) to (n) of FIG. 51 show the calibration curves for this standard sample, respectively.

As can be seen from FIG. 51, the peak heights and peak areas of the chromatograms detected by the ICPMS with the ultraviolet 210 nm and 280 nm, respectively, exhibit good linearity (correlation coefficient R2>0.996). Therefore, the elemental quantities can be evaluated with the peak area and peak height of LC-ICPMS chromatogram.

TABLE 5

| | |
|---|---|
| Column | Phenomenex Yarra SEC-X300 (300 mmL. × 4.6 mm I.D., 1.8 μm, MW range 10k-700 kDa) |
| Mobile phase | 100 mmol/L aqueous ammonium acetate solution, near pH 6 |
| Mobile phase flow rate | 0.3 mL/min (pressure 18.2 MPa) |
| Column temperature | 35° C. |
| Injection volume | 10 μL (SIL wash solution: water) |
| Sample | Wako Cyanocobalamin, C63H88CoN14O14P, MW 1355.38 (Vitamin B12, VB12) SIGMA Myoglobin from equine heart, MW 17 kDa Dissolve in the mobile phase |
| Detector | Shimadzu UV detector SPD-20AV Semi-micro temperature control cell |
| | Lamp: D$_2$ |
| | Wavelength: 210, 280 nm |
| | Sampling: 2 Hz |

TABLE 5-continued

Figure 2:
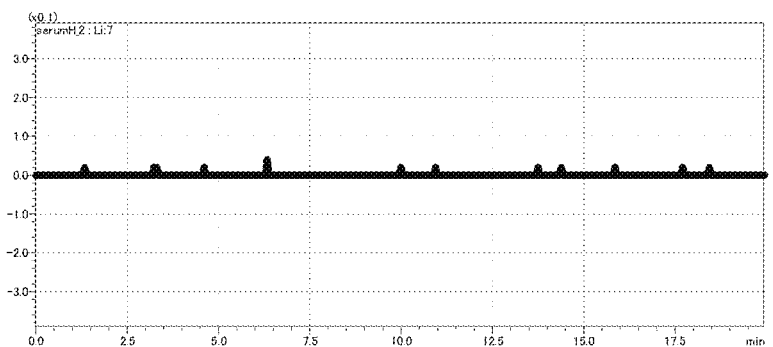
FIG. 2 is a chromatogram of specified 47 types of elements measured in Example 2.
Figure 3:
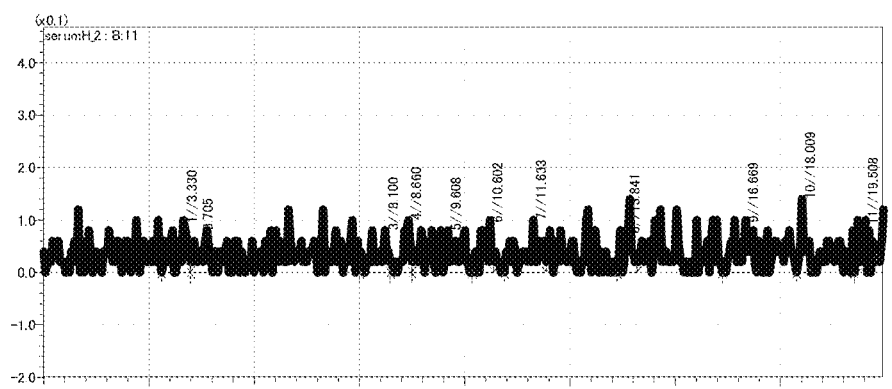
FIG. 3 is a chromatogram of specified 47 types of elements measured in Example 2.
Figure 4:
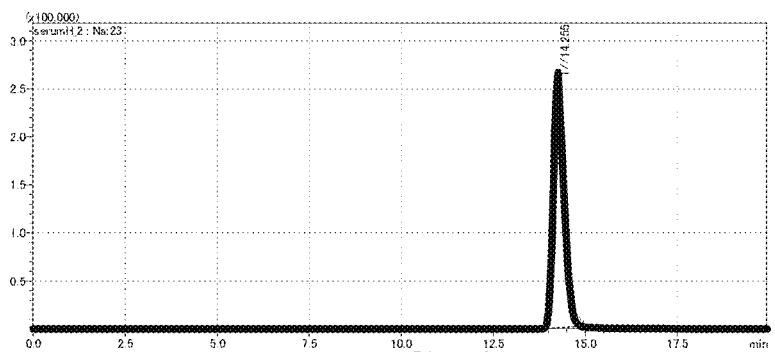
FIG. 4 is a chromatogram of specified 47 types of elements measured in Example 2.
Figure 5:
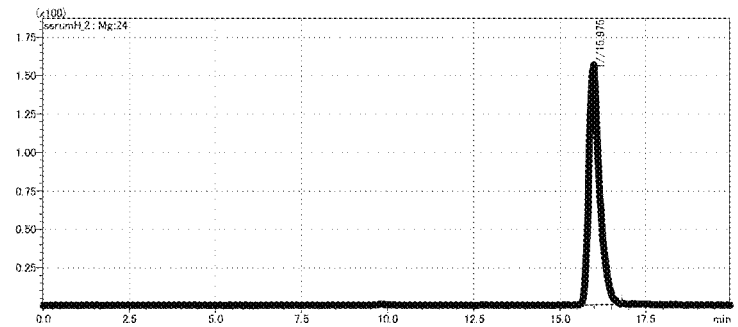
FIG. 5 is a chromatogram of specified 47 types of elements measured in Example 2.
Figure 6:
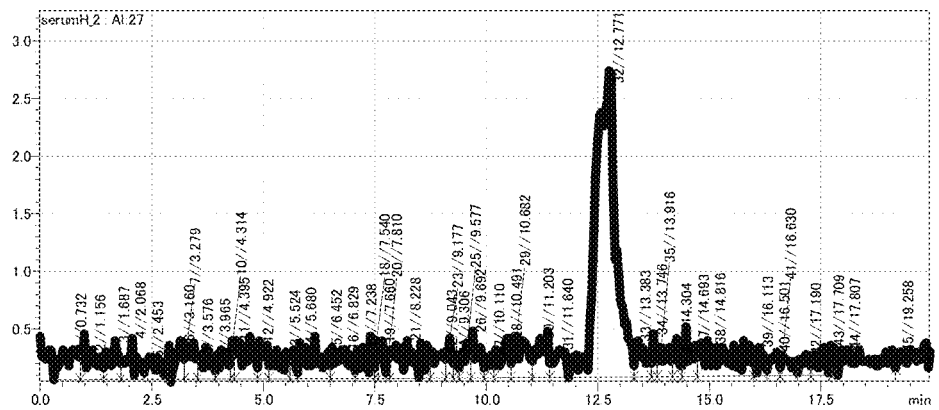
FIG. 6 is a chromatogram of specified 47 types of elements measured in Example 2.
Figure 7:
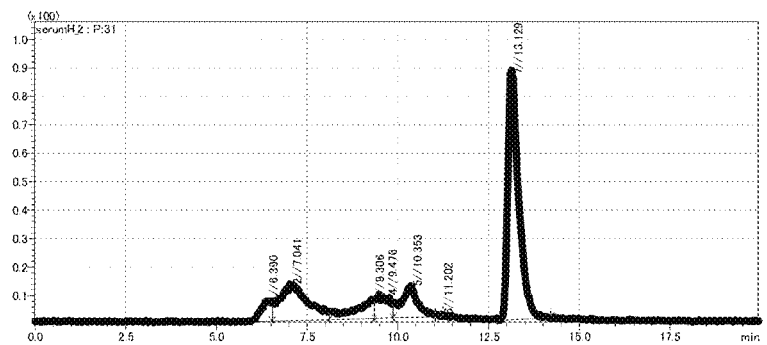
FIG. 7 is a chromatogram of specified 47 types of elements measured in Example 2.
Figure 8:
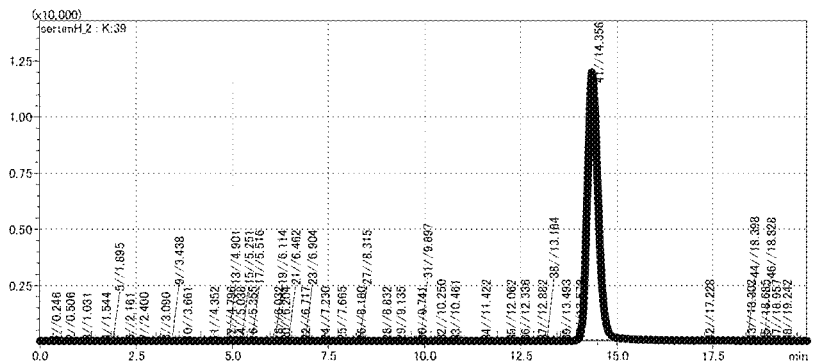
FIG. 8 is a chromatogram of specified 47 types of elements measured in Example 2.
Figure 9:
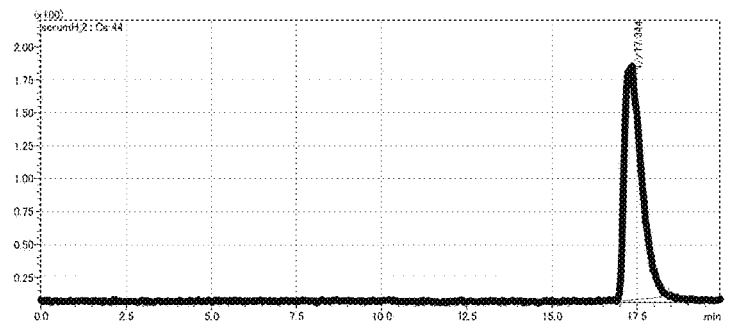
FIG. 9 is a chromatogram of specified 47 types of elements measured in Example 2.
Figure 10:
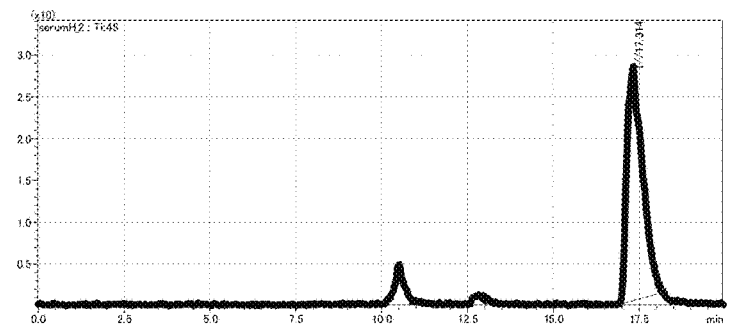
FIG. 10 is a chromatogram of specified 47 types of elements measured in Example 2.
Figure 11:
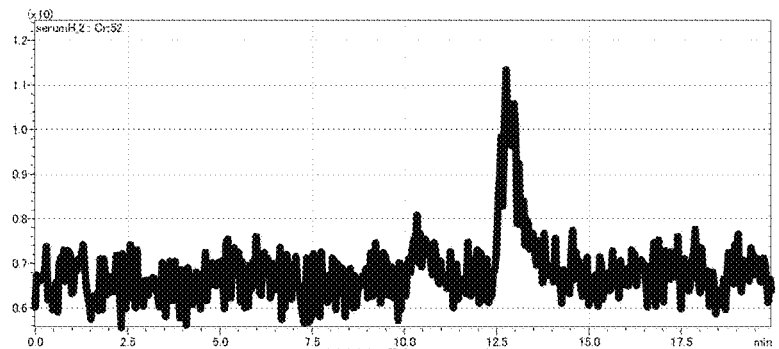
FIG. 11 is a chromatogram of specified 47 types of elements measured in Example 2.
Figure 12:
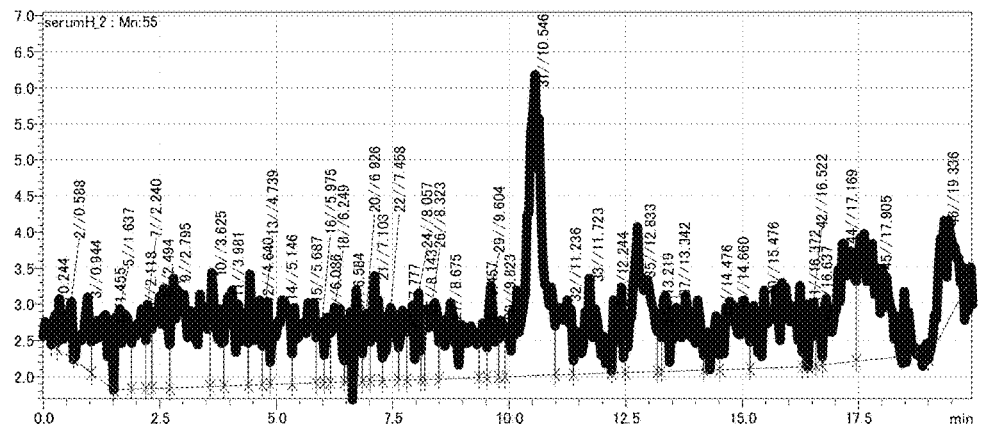
FIG. 12 is a chromatogram of specified 47 types of elements measured in Example 2.
Figure 13:
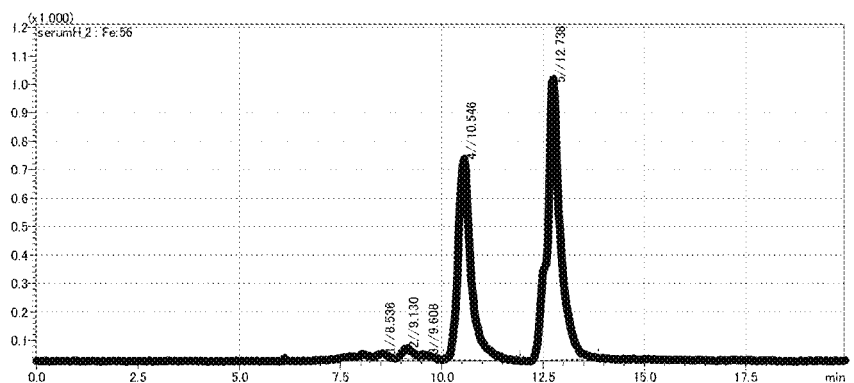
FIG. 13 is a chromatogram of specified 47 types of elements measured in Example 2.
Figure 14:
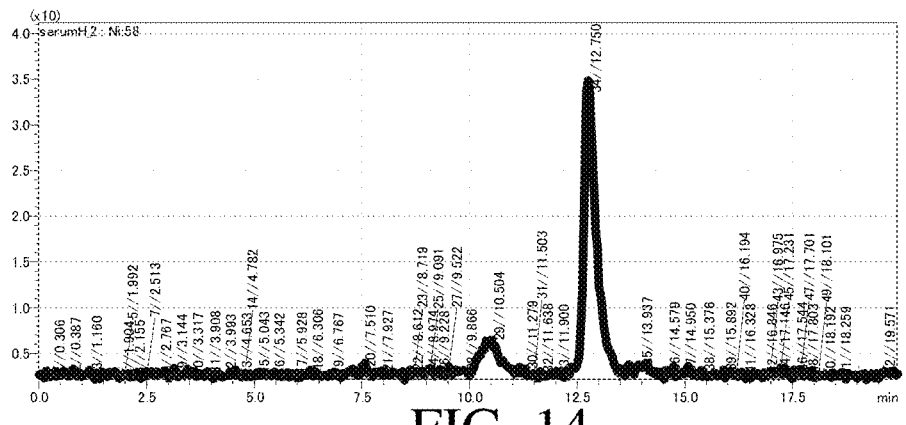
FIG. 14 is a chromatogram of specified 47 types of elements measured in Example 2.
Figure 15:
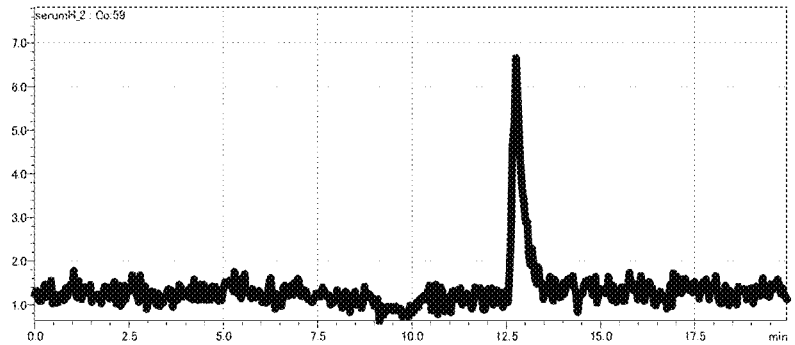
FIG. 15 is a chromatogram of specified 47 types of elements measured in Example 2.
Figure 16:
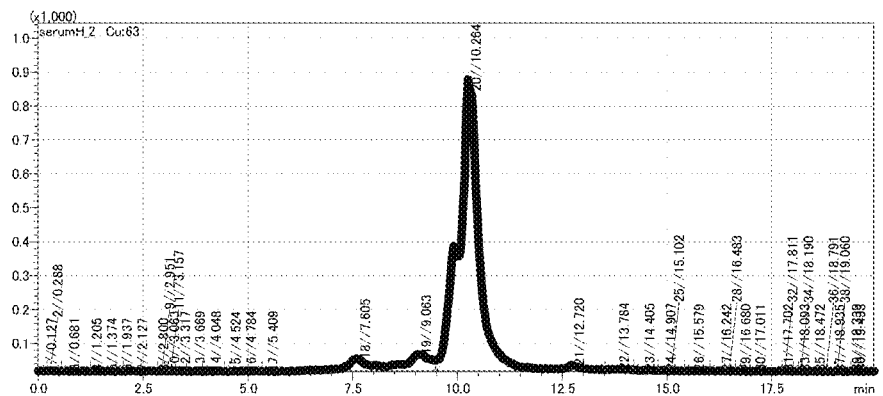
FIG. 16 is a chromatogram of specified 47 types of elements measured in Example 2.
Figure 17:
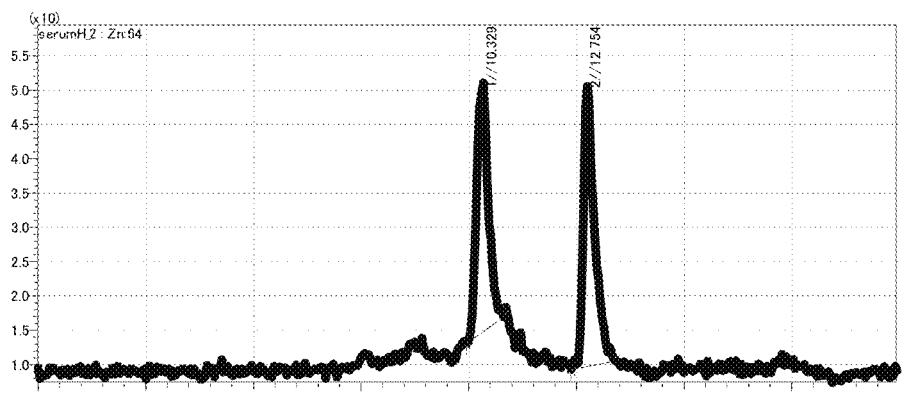
FIG. 17 is a chromatogram of specified 47 types of elements measured in Example 2.
Figure 18:
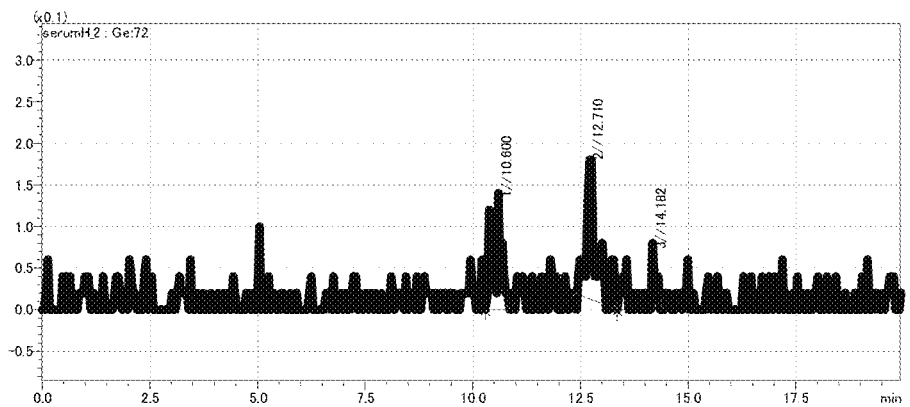
FIG. 18 is a chromatogram of specified 47 types of elements measured in Example 2.
Figure 25:
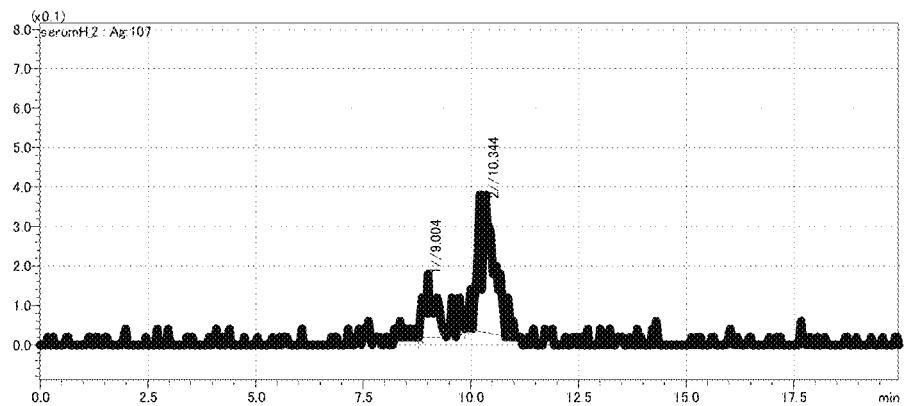
FIG. 25 is a chromatogram of specified 47 types of elements measured in Example 2.
Figure 26:
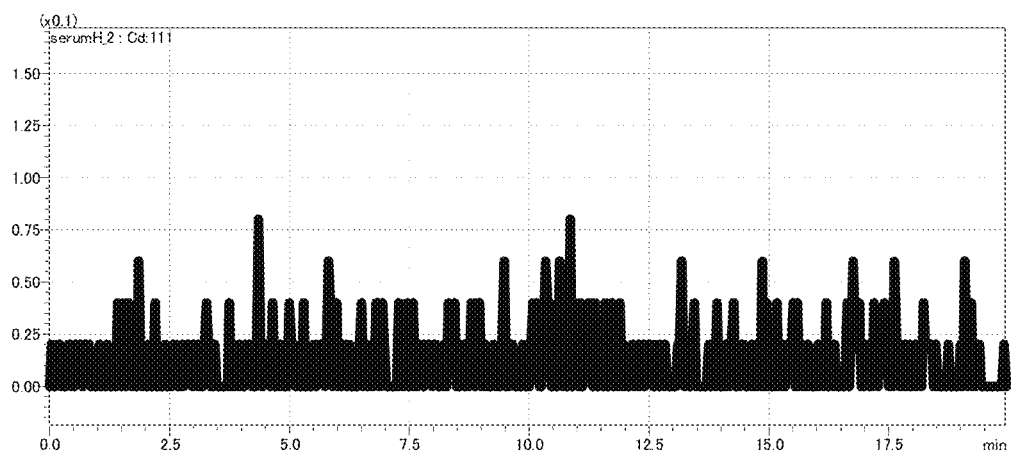
FIG. 26 is a chromatogram of specified 47 types of elements measured in Example 2.
Figure 27:
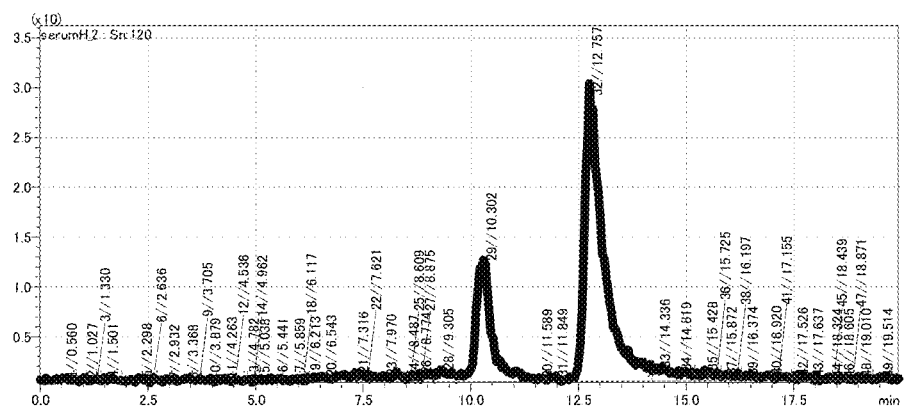
FIG. 27 is a chromatogram of specified 47 types of elements measured in Example 2.
Figure 28:
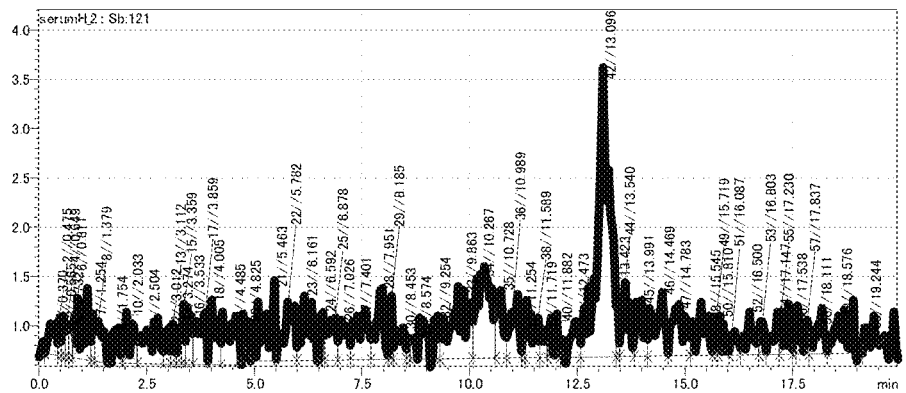
FIG. 28 is a chromatogram of specified 47 types of elements measured in Example 2.
Figure 29:
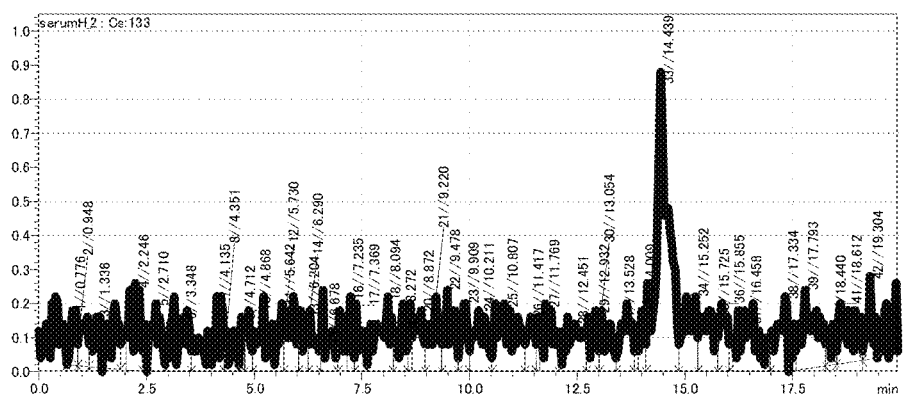
FIG. 29 is a chromatogram of specified 47 types of elements measured in Example 2.
Figure 30:
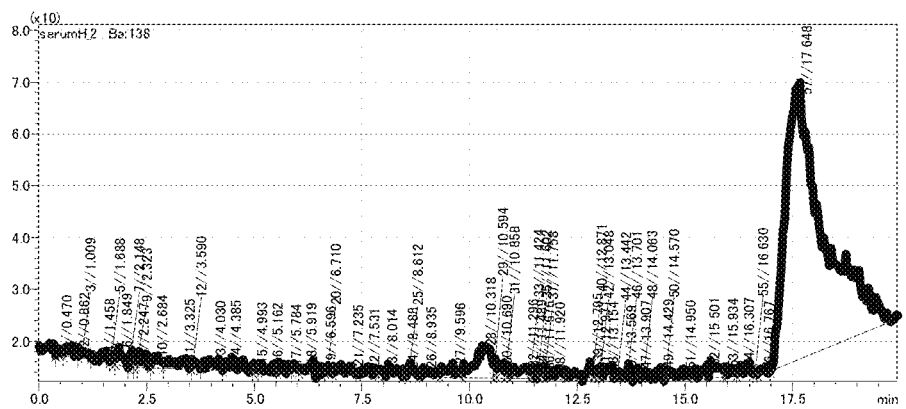
FIG. 30 is a chromatogram of specified 47 types of elements measured in Example 2.
Figure 31:
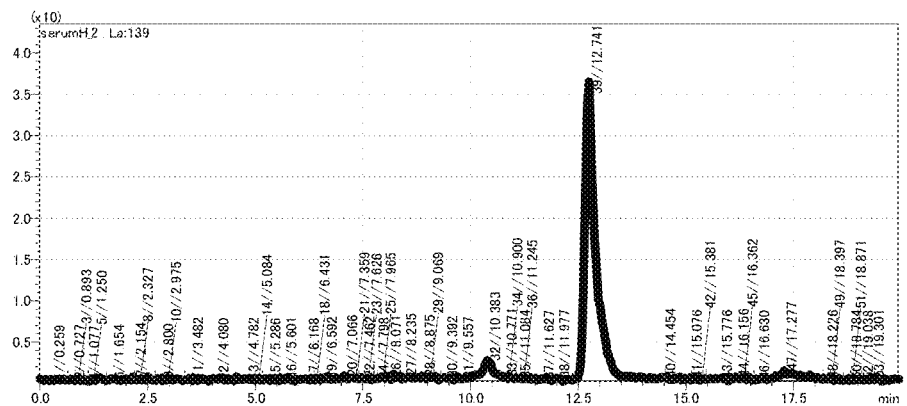
FIG. 31 is a chromatogram of specified 47 types of elements measured in Example 2.
Figure 32:
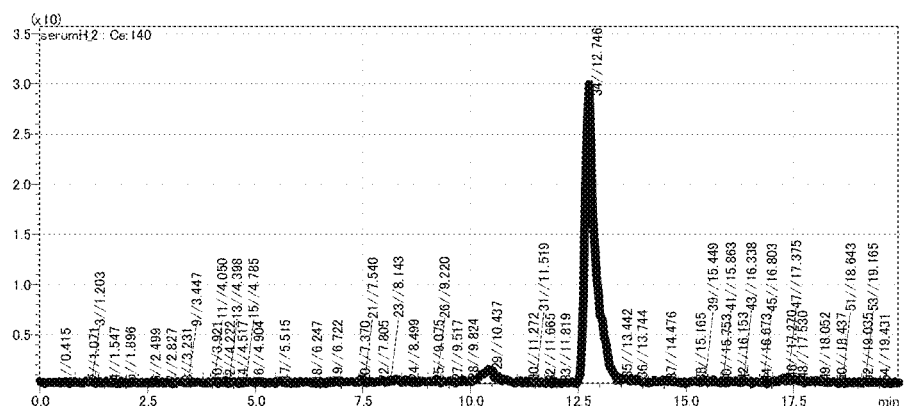
FIG. 32 is a chromatogram of specified 47 types of elements measured in Example 2.
Figure 33:
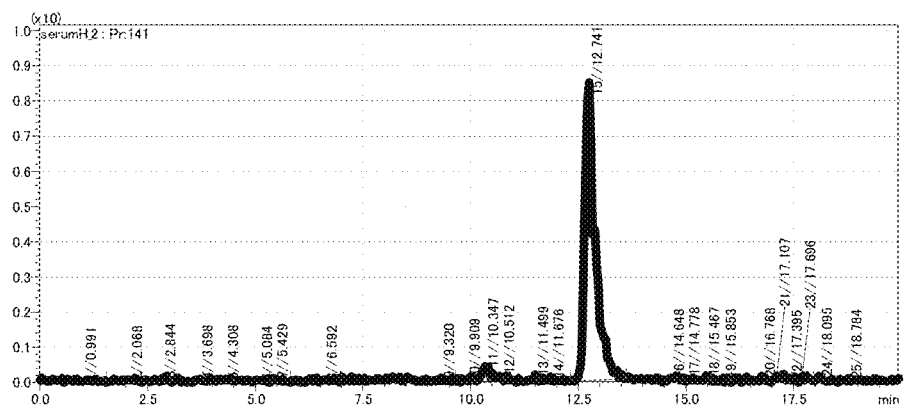
FIG. 33 is a chromatogram of specified 47 types of elements measured in Example 2.
Figure 34:
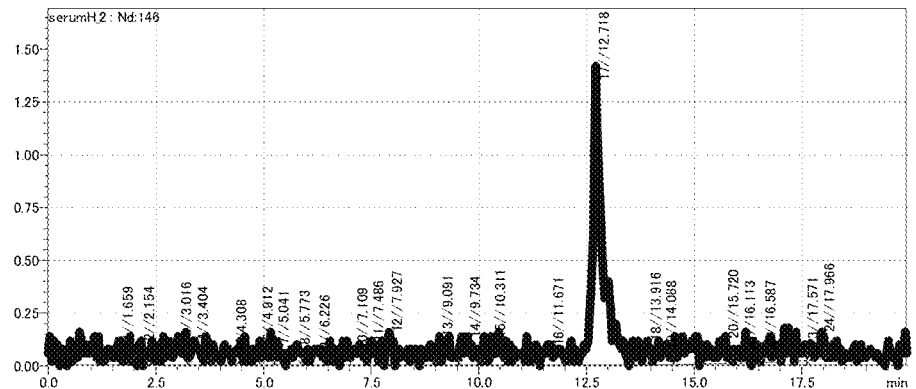
FIG. 34 is a chromatogram of specified 47 types of elements measured in Example 2.
Figure 35:
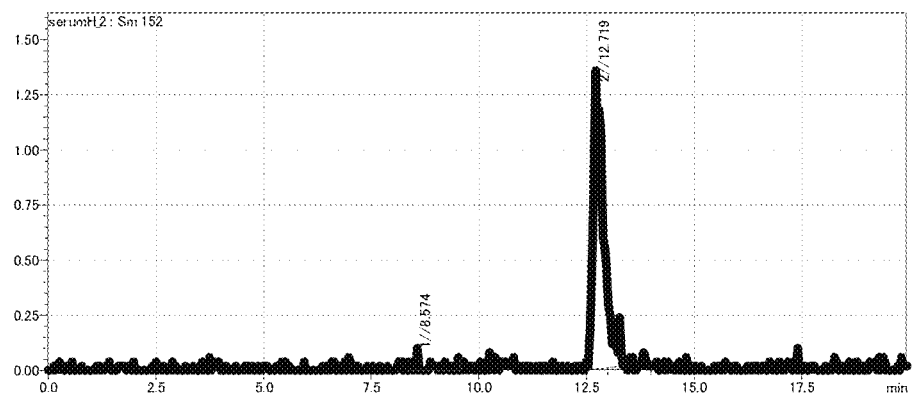
FIG. 35 is a chromatogram of specified 47 types of elements measured in Example 2.
Figure 36:
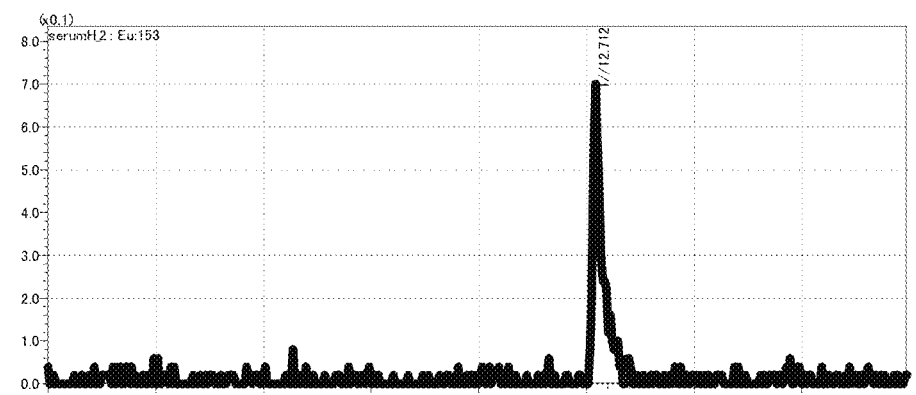
FIG. 36 is a chromatogram of specified 47 types of elements measured in Example 2.
Figure 37:
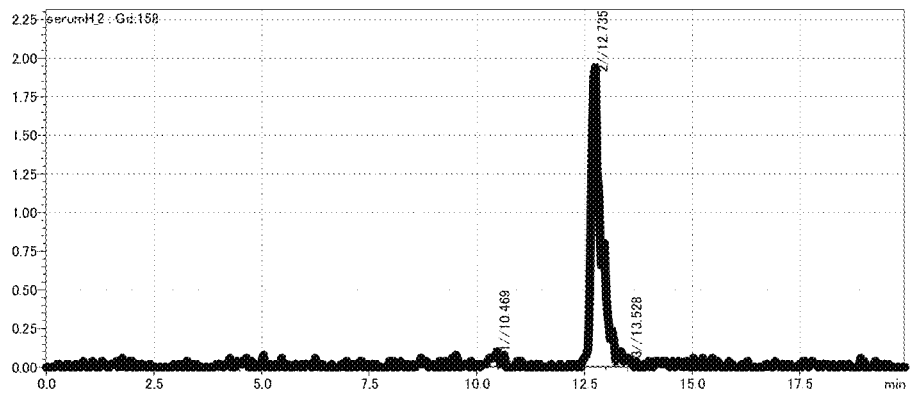
FIG. 37 is a chromatogram of specified 47 types of elements measured in Example 2.
Figure 38:
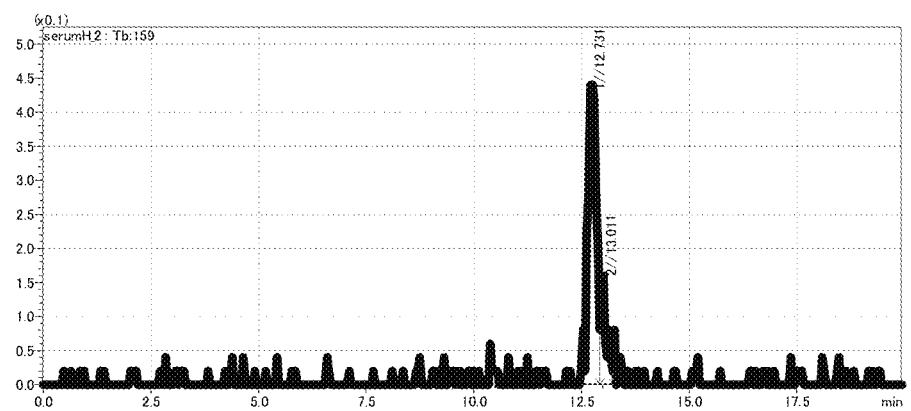
FIG. 38 is a chromatogram of specified 47 types of elements measured in Example 2.
Figure 39:
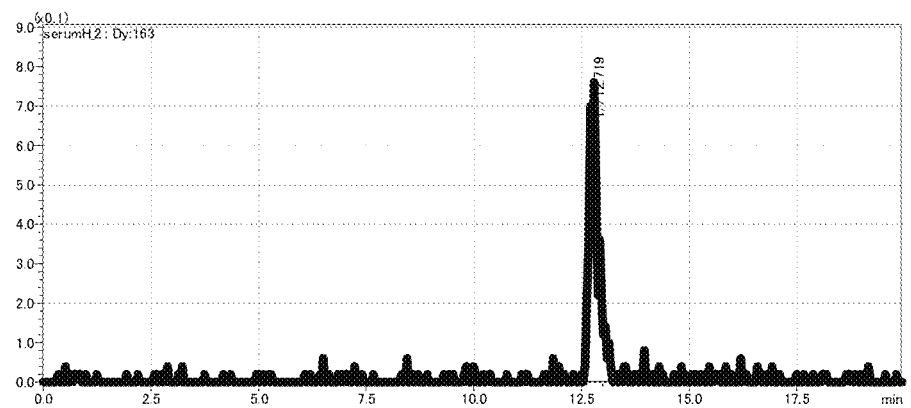
FIG. 39 is a chromatogram of specified 47 types of elements measured in Example 2.
Figure 40:
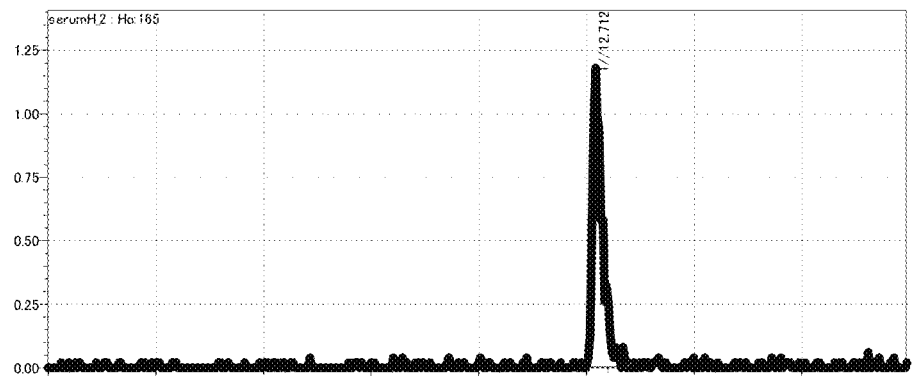
FIG. 40 is a chromatogram of specified 47 types of elements measured in Example 2.
Figure 41:
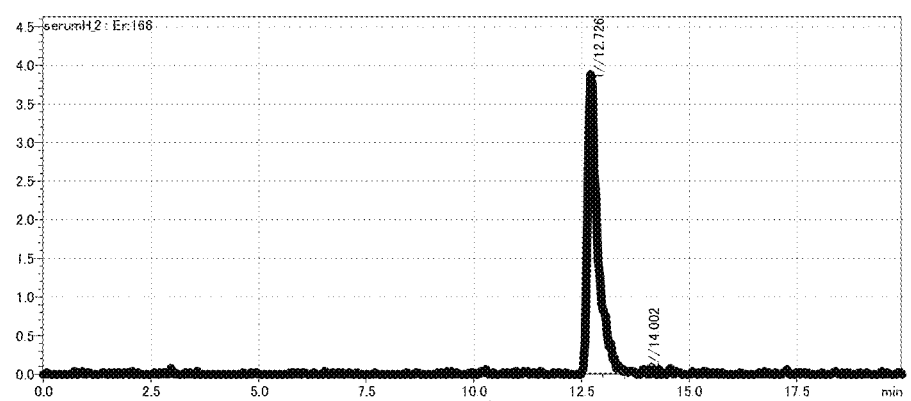
FIG. 41 is a chromatogram of specified 47 types of elements measured in Example 2.
Figure 42:
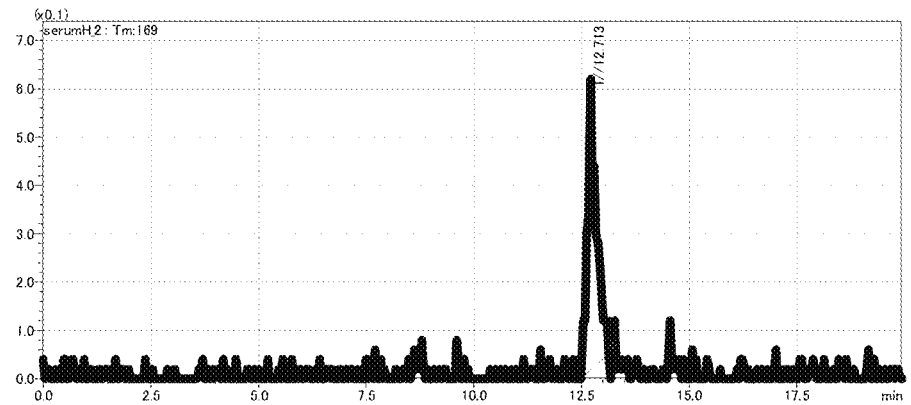
FIG. 42 is a chromatogram of specified 47 types of elements measured in Example 2.
Figure 43:
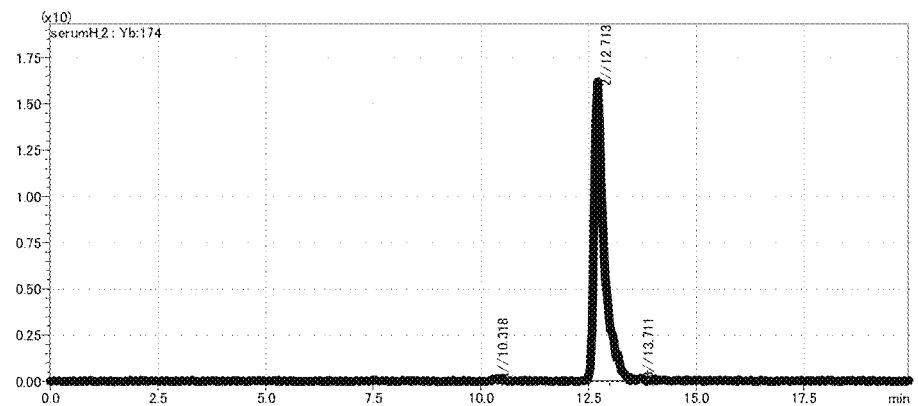
FIG. 43 is a chromatogram of specified 47 types of elements measured in Example 2.
Figure 44:
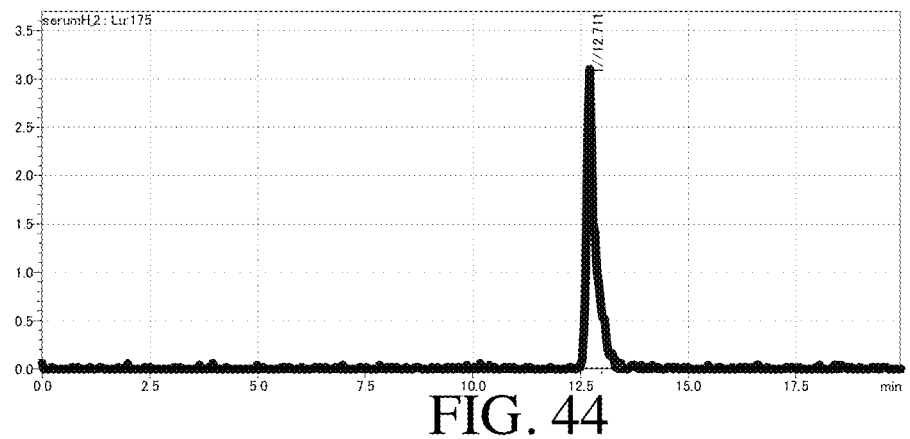
FIG. 44 is a chromatogram of specified 47 types of elements measured in Example 2.
Figure 45:
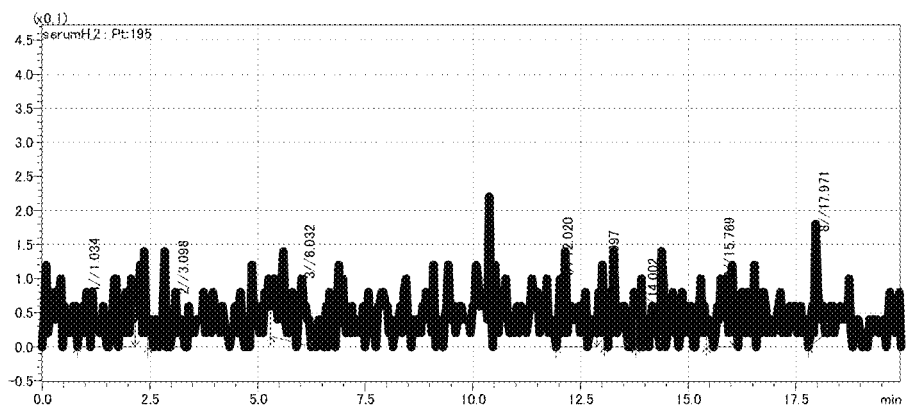
FIG. 45 is a chromatogram of specified 47 types of elements measured in Example 2.
Figure 46:
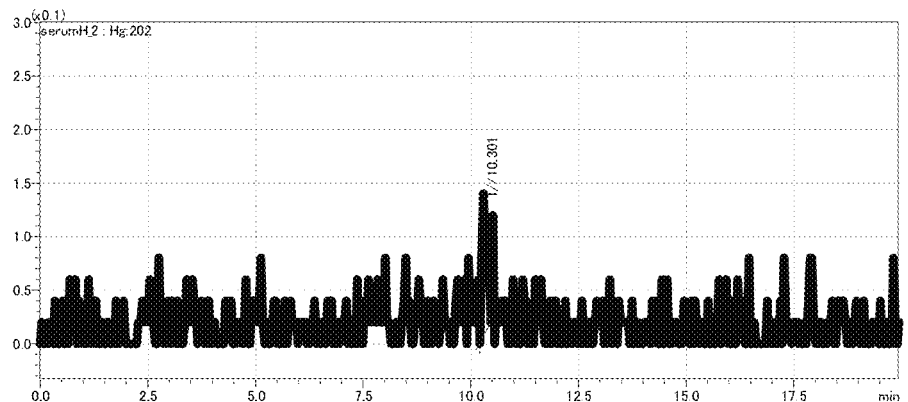
FIG. 46 is a chromatogram of specified 47 types of elements measured in Example 2.
Figure 47:
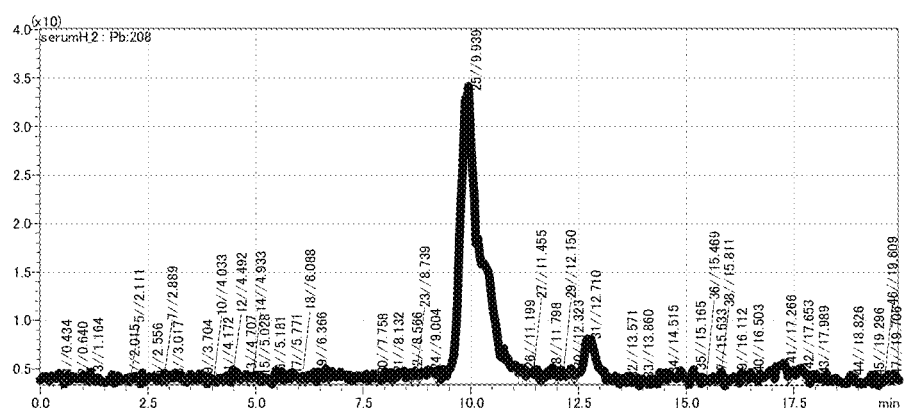
FIG. 47 is a chromatogram of specified 47 types of elements measured in Example 2.
Figure 48:
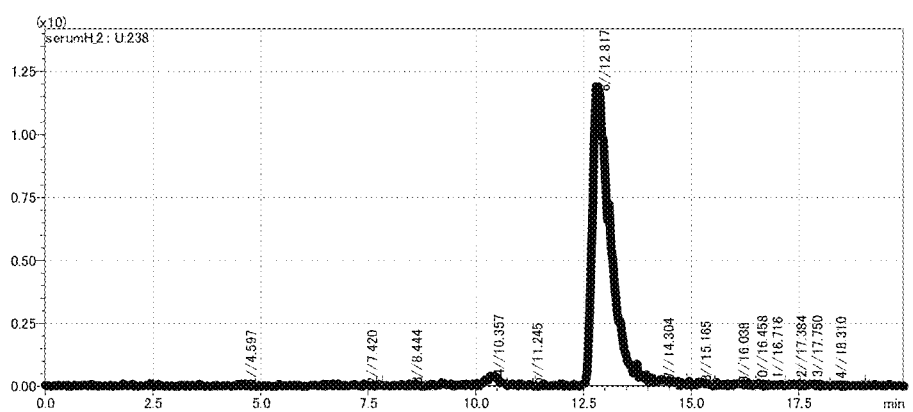
FIG. 48 is a chromatogram of specified 47 types of elements measured in Example 2.

| | |
|---|---|
| | Cell temperature: 40° C. |
| | Capture time: 21 min |
| ICPMS | See FIG. 2-2 |
| | Capture time: 20 min |

| Detected ion: | element m/z | Dwell time (sec) |
|---|---|---|
| Fe | 56 | 0.100 |
| Co | 59 | 0.100 |

| | |
|---|---|
| Measurement time | 21 min |

The invention claimed is:

1. A method for analyzing a metalloprotein in a biological sample, the metalloprotein being a complex in which a biomolecule and a metal element bind to each other, the method comprising:
   treating the biological sample that has been subjected to a pretreatment by liquid chromatography to separate the metalloprotein;
   detecting the separated metalloprotein by a UV detector;
   analyzing the separated metalloprotein by inductively coupled plasma mass spectrometry after detecting the separated metalloprotein by the UV detector;
   comparing a detection signal of the UV detector with a detection signal of the inductively coupled plasma mass spectrometry; and
   determining that the inductively coupled plasma mass spectrometry is failed when an intensity of the detection signal of the inductively coupled plasma mass spectrometry is smaller than an intensity of the detection signal of the UV detector,
   wherein an ammonium acetate solution is used as a mobile phase.

2. The method for analyzing a metalloprotein in a biological sample as recited in claim 1,
   wherein the liquid chromatography is size exclusion chromatography.

3. The method for analyzing a metalloprotein in a biological sample as recited in claim 2,
   wherein a pH value of the ammonium acetate solution is between 6 and 7.

4. The method for analyzing a metalloprotein in a biological sample as recited in claim 1,
   wherein a concentration of the ammonium acetate solution is 25 mM to 100 mM.

5. The method for analyzing a metalloprotein in a biological sample as recited in claim 1,
   wherein immunoaffinity chromatography is used in the pretreatment.

6. The method for analyzing a metalloprotein in a biological sample as recited in claim 1,
   wherein the separated metalloprotein is further analyzed by electrospray ionization mass spectrometry when analyzing by the inductively coupled plasma mass spectrometry.

7. The method for analyzing a metalloprotein in a biological sample as recited in claim 1,
   wherein the metal element is K, P, Na, Ca, Mg, Al, As, Hg, Pb, Cd, Ti, Ag, Ba, Zn, Cr, Mn, Cu, Rb, Fe, Ge, Se, Sr, Co, Ni, Mo, Sn, Sb, Pt, Cs, U, La, Ce, Pr, Nd, Sm, En, Gd, Tb, Dy, Ho, Er, Tm, Yb, Ln, Y, Li, or B.

* * * * *